… … … … … … United States Patent [19] … … [11] Patent Number: 5,206,166
Payne et al. … … [45] Date of Patent: Apr. 27, 1993

[54] GENES ENCODING LEPIDOPTERAN-ACTIVE TOXINS AND TRANSFORMED HOSTS

[75] Inventors: Jewel Payne, San Diego; August J. Sick, Oceanside, both of Calif.

[73] Assignee: Mycogen Corporation, San Diego, Calif.

[21] Appl. No.: 904,243

[22] Filed: Jun. 25, 1992

Related U.S. Application Data

[60] Division of Ser. No. 451,389, Dec. 14, 1989, Pat. No. 5,164,180, which is a continuation-in-part of Ser. No. 353,860, May 18, 1989, abandoned.

[51] Int. Cl.$^5$ .................. C12N 1/21; C12N 15/32; C12N 15/70
[52] U.S. Cl. .................. 435/252.3; 435/252.31; 435/252.33; 435/252.34; 435/252.35; 435/320.1; 536/23.71; 935/22; 935/27; 935/29

[58] Field of Search ............ 424/93 L; 435/71.2, 435/91, 170, 172.1, 172.2, 172.3, 252.1, 252.2, 252.3, 252.31, 252.33, 252.34, 252.35, 320.1; 536/27; 935/6, 9, 22, 27, 29

[56] References Cited

U.S. PATENT DOCUMENTS 4,467,036  8/1984  Schnepf et al. .................. 435/320.1

Primary Examiner—Richard A. Schwartz
Assistant Examiner—Gary L. Brown
Attorney, Agent, or Firm—Saliwanchik & Saliwanchik

[57] ABSTRACT

Novel *Bacillus thuringiensis* genes encoding toxins which are active against lepidopteran insects have been cloned from novel lepidopteran-active *B. thuringiensis* microbes. The DNA encoding the *B. thuringiensis* toxins can be used to transform various prokaryotic and eukaryotic microbes to express the *B. thuringiensis* toxins. These recombinant microbes can be used to control lepidopteran insects in various environments.

10 Claims, 45 Drawing Sheets

```
                        5                      10                     15
  1 Met Glu Asn Asn Ile Glu Asn Gln Cys Ile Pro Tyr Asn Cys Leu
 16 Asn Asn Pro Glu Val Glu Ile Leu Gly Ile Glu Arg Ser Asn Ser
 31 Asn Val Ala Ala Glu Ile Gly Leu Gly Leu Ser Arg Leu Leu Val
 46 Ser Arg Ile Pro Leu Gly Asp Phe Ile Leu Gly Leu Phe Asp Val
 61 Ile Trp Gly Ala Ile Gly Pro Ser Gln Trp Asp Ile Phe Leu Glu
 76 Gln Ile Glu Leu Leu Ile Gly Gln Arg Ile Glu Glu Phe Ala Arg
 91 Asn Gln Ala Ile Ser Arg Leu Gln Gly Leu Ser Asn Leu Tyr Arg
106 Ile Tyr Thr Asn Ala Phe Lys Asn Trp Glu Val Asp Pro Thr Asn
121 Pro Ala Leu Arg Glu Glu Met Arg Ile Gln Phe Asn Asp Met Asn
136 Ser Ala Leu Thr Thr Ala Ile Pro Leu Phe Ser Val Gln Gly Tyr
151 Glu Ile Pro Leu Leu Ser Val Tyr Val Gln Ala Ala Asn Leu His
166 Leu Ser Val Leu Arg Asp Val Ser Val Phe Gly Gln Arg Trp Gly
181 Phe Asp Val Ala Thr Ile Asn Ser Arg Tyr Asn Asp Leu Thr Arg
196 Leu Ile Gly Glu Tyr Thr Asp Tyr Ala Val Arg Trp Tyr Asn Thr
211 Gly Leu Asn Arg Leu Pro Arg Asn Glu Gly Val Arg Gly Trp Ala
226 Arg Phe Asn Arg Phe Arg Arg Glu Leu Thr Ile Ser Val Leu Asp
241 Ile Ile Ser Phe Phe Gln Asn Tyr Asp Ser Arg Leu Tyr Pro Ile
256 Pro Thr Ile Tyr Gln Leu Thr Arg Glu Val Tyr Thr Asp Pro Val
```

```
     10         20         30         40         50         60
  1 ATGGAGAATA ATATTGAAAA TCAATGCATA CCTTACAATT GTTAAATAA TCCTGAAGTA
 61 GAGATATTAG GGATTGAAAG GTCAAATAGT AACGTAGCAG CAGAAATCGG CTTGGGGCTT
121 AGTCGTCTGC TCGTTTCCCG AATTCCACTA GGGGATTTTA TACTTGGCTT GTTTGATGTA
181 ATATGGGGGG CTATAGGTCC TTCACAATGG GATATATTTT TAGAGCAAAT TGAGCTATTG
241 ATCGGCCAAA GAATAGAGGA ATTCGCTAGG AATCAGGCAA TTTCTAGATT ACAAGGGCTA 310        320        330        340        350        360
301 AGCAATCTTT ACCGAATTTA CACAAATGCT TTTAAAAACT GGGAAGTAGA TCCTACTAAT
361 CCAGCATTAA GAGAAGAGAT GCGTATTCAA TTTAATGACA TGAACAGTGC TCTTACAACA
421 GCTATTCCTC TTTTTTCAGT TCAAGGTTAT GAAATTCCTC TTTTATCAGT ATATGTTCAA
481 GCTGCAAATT TACATTTATC GGTTTTTGAGA GATGTTTCAG TGTTTGGACA ACGTTGGGGA
541 TTTGATGTAG CAACAATCAA TAGTCGTTAT AATGATTTAA CTAGGCTTAT TGGCGAATAT 610        620        630        640        650        660
601 ACTGATTATG CTGTACGTTG GGTATAATACG GGGTTAAATC GTTACCACG TAATGAAGGG
661 GTACGAGGAT GGGCAAGATT TAATAGGTTT AGAAGAGAGT TAACAATATC AGTATTAGAT
721 ATTATTTCTT TTTTCCAAAA TTACGATTCT AGATTATATC CAATTCCGAC AATCTATCAA
781 TTAACGCGGG AAGTATATAC AGATCCGGTA ATTAATATAA CTGATTATAG AGTTACCCCA
841 AGTTTCGAGA GTATTGAAAA TTCAGCTATT AGAAGTCCCC ATCTTATGGA TTTCTTAAAT
```

Figure 2A

```
            910        920        930        940        950        960
 901 AATATAATTA TTGACACTGA TTTAATTAGA GGCGTTCACT ATTGGGCGGG GCATCGTGTA
 961 ACTTCTCATT TTACCGGTAG TTCGCAAGTG ATAAGCTCCC CTCAATACGG GATAACTGCA
1021 AACGCAGAAC CGAGTCGAAC TATTGCTCCT AGCACTTTTC CAGGTCTTAA TCTATTTTAT
1081 AGAACACTAT CAGACCCTTT CTTCCGAAGA TCCGATAATA TTATGCCAAC ATTAGGAATA
1141 AATGTAGTGC AGGGGGTAGG ATTCATTCAA CCAAATAATG GTGAAGTTCT ATATAGAAGG 1210       1220       1230       1240       1250       1260
1201 AGAGGAACAG TAGATTCTCT TGATGAGTTG CCAATTGACG GTGAGAATTC ATTAGTTGGA
1261 TATAGTCATA GATTAAGTCA CGTTACATTA ACCAGGTCGT TATATAATAC TAATATAACT
1321 AGCTTGCCAA CATTTGTTTG GACACATCAC AGTGCTACTG ATCGAAATAT AATCTATCCG
1381 GATGTAATTA CACAAATACC ATTGGTAAAA TCATTCTCCC TTACTTCAGG TACCTCTGTA
1441 GTCAGAGGCC CAGGATTTAC AGGAGGGGAT ATCATCCGAA CTAACGTTAA TGGTAATGTA 1510       1520       1530       1540       1550       1560
1501 CTAAGTATGA GTCTTAATTT TAGTAATACA TCATTACAGC GGTATGCGCT GAGAGTTCGT
1561 TATGCTGCTT CTCAAACAAT GGTCATGAGA GTAAATGTTG GAGGGAGTAC TACTTTTGAT
1621 CAAGGATTCC CTAGTACTAT GAGTGCAAAT GGGTCTTTGA CATCTCAATC ATTTAGATTT
1681 GCAGAATTTC CTGTAGGCAT TAGTACATCT GGCAGTCAAA CTGCTGGAAT AAGTATAAGT
1741 AATAATCCAG GTAGACAAAC GTTCACTTA GATAGAATTG AATTTATCCC AGTTGATGCA
```

Figure 2B

```
           1810       1820       1830       1840       1850       1860
1801 ACATTTGAAG CAGAATATGA TTTAGAAAGA GCACAAAAGG CGGTGAATTC GCTGTTTACT
1861 TCTTCCAATC AAATCGAGTT AAAAACAGAT GTGACGGATT ATCATATTGA TCAAGTATCC
1921 AATTTAGTAG ATTGTTTATC CGATGAATTT TGTCTGGATG AAAAGCGAGA ATTGTCCGAG
1981 AAAGTCAAAC ATGCGAAGCG ACTCAGTGAT GAGCGGAATT TACTTCAAGA TCCAAACTTC
2041 AGAGGGATCA ATAGGCAACC AGACCGTGGC TGGAGAGGAA GTACGGATAT TACCATCCAA
           2110       2120       2130       2140       2150       2160
2101 GGAGGAGATG ACGTATTCAA AGAGAATTAC GTCACACTAC CAGGTACCTT TGATGAGTGC
2161 TATCCAACGT ATTTGTATCA AAAATATAGAT GAGTCGAAAT TAAAAGCCTA TAACCGTTAC
2221 CAATTAAGAG GGTATATCGA AGATAGTCAA GACTTAGAAA TCTATTTAAT TCGCTACAAT
2281 GCAAAACACG AAACAGTAAA TGTACCAGGT ACGGGTTCCT TATGGCCGCT TTCAGTCGAA
2341 AGTCCAATTG GAAGGTGTGG AGAACCGAAT CGGTGTGTGC CACACCCTTGA ATGGAATCCT
```

Figure 2C

```
      2410       2420       2430       2440       2450       2460
2401 GATTTAGATT GTTCCTGCAG AGACGGGGAA AAATGTGCAC ATCATTCCCA TCATTTCTCC
2461 TTGGACATTG ATGTTGGATG CACAGACTTG CAAGAGGATC TAGGCGTGTG GGTTGTATTC
2521 AAGATTAAGA CGCAGGAAGG TTATGCAAGA TTAGGAAATC TGGAATTTAT CGAAGAGAAA
2581 CCATTAATTG GAGAAGCACT GTCTCGTGTG AAGAGAGCGG AAAAAAATG GAGAGACAAA
2641 CGGGAAAAAC TACAATTGGA AACAAAACGA GTATATACAG AGGCAAAAGA AGCTGTGGAT 2710       2720       2730       2740       2750       2760
2701 GCTTTATTCG TAGATTCTCA ATATGATAGA TTACAAGCAG ATACAAACAT TGGTATGATT
2761 CATGCGGCAG ATAGACTTGT TCATCAGATC CACGAGGCTT ATCTTCCAGA ACTACCTTTC
2821 ATTCCAGGAA TAAATGTGGT GATTTTTGAA GAATTAGAAA ACCGTATTTC TACTGCATTA
2881 TCCCTATATG ATGCGAGAAA TGTCATTAAA AATGGCGATT TCAATAATGG CTTATCATGC
2941 TGGAACGTGA AAGGGCATGT AGATGTAGTA GAACAAAACA ACCACCGTTC GGTCCTTGTT
```

Figure 2D

```
                        5                   10                  15
  1 Met Glu Asn Asn Ile Glu Asn Gln Cys Ile Pro Tyr Asn Cys Leu
 16 Asn Asn Pro Glu Val Glu Ile Leu Gly Ile Glu Arg Ser Asn Ser
 31 Asn Val Ala Ala Glu Ile Gly Leu Gly Leu Ser Arg Leu Leu Val
 46 Ser Arg Ile Pro Leu Gly Asp Phe Ile Leu Gly Leu Phe Asp Val
 61 Ile Trp Gly Ala Ile Gly Pro Ser Gln Trp Asp Ile Phe Leu Glu
 76 Gln Ile Glu Leu Leu Ile Gly Gln Arg Ile Glu Gly Phe Ala Arg
 91 Asn Gln Ala Ile Ser Arg Leu Gln Gly Leu Ser Asn Leu Tyr Arg
106 Ile Tyr Thr Asn Ala Phe Lys Asn Trp Glu Val Asp Pro Thr Asn
121 Pro Ala Leu Arg Glu Glu Met Arg Ile Gln Phe Asn Asp Met Asn
136 Ser Ala Leu Thr Thr Ala Ile Pro Leu Phe Ser Val Gln Gly Tyr
151 Glu Ile Pro Leu Leu Ser Val Tyr Val Gln Ala Ala Asn Leu His
166 Leu Ser Val Leu Arg Asp Val Ser Val Phe Gly Gln Arg Trp Gly
181 Phe Asp Val Ala Thr Ile Asn Ser Arg Tyr Asn Asp Leu Thr Arg
196 Leu Ile Gly Glu Tyr Thr Asp Tyr Ala Val Arg Trp Tyr Asn Thr
211 Gly Leu Asn Arg Leu Pro Arg Asn Glu Leu Thr Ile Ser Val Leu Asp
226 Arg Phe Asn Arg Arg Phe Gln Asn Tyr Asp Ser Arg Leu Tyr Pro Ile
241 Ile Ile Ser Phe Phe Gln Asn Tyr Asp Ser Arg Leu Tyr Pro Ile
256 Pro Thr Ile Tyr Gln Leu Thr Arg Glu Val Tyr Thr Asp Pro Val
```

Figure 3A

```
271 Ile Asn Ile Thr Asp Tyr Arg Val Thr Pro Ser Phe Glu Ser Ile
286 Glu Asn Ser Ala Ile Arg Ser Pro His Leu Met Asp Phe Leu Asn
301 Asn Ile Ile Asp Thr Asp Leu Ile Arg Gly Val His Tyr Trp
316 Ala Gly His Arg Val Thr Ser His Phe Gly Ser Ser Gln Val
331 Ile Ser Ser Pro Gln Tyr Gly Ile Thr Ala Asn Ala Glu Pro Ser
346 Arg Thr Ile Ala Pro Ser Thr Phe Pro Gly Leu Asn Leu Phe Tyr
361 Arg Thr Leu Ser Asp Pro Phe Phe Arg Arg Ser Asp Asn Ile Met
376 Pro Thr Leu Gly Ile Asn Val Val Gln Gly Val Gly Phe Ile Gln
391 Pro Asn Asn Gly Glu Val Leu Tyr Arg Arg Arg Gly Thr Val Asp
406 Ser Leu Asp Glu Leu Pro Ile Asp Gly Glu Asn Ser Leu Val Gly
421 Tyr Ser His Arg Leu Ser His Val Thr Leu Thr Arg Ser Leu Tyr
436 Asn Thr Asn Ile Thr Ser Leu Pro Thr Phe Val Trp Thr His His
451 Ser Ala Thr Asp Arg Asn Ile Ile Tyr Pro Asp Val Ile Thr Gln
466 Ile Pro Leu Val Lys Ser Phe Ser Leu Thr Ser Gly Thr Ser Val
481 Val Arg Gly Pro Gly Phe Thr Gly Gly Asp Ile Ile Arg Thr Asn
496 Val Asn Gly Asn Val Leu Ser Met Ser Leu Asn Phe Ser Asn Thr
511 Ser Leu Gln Arg Tyr Arg Val Arg Val Arg Tyr Ala Ala Ser Gln
526 Thr Met Val Met Arg Val Asn Val Gly Gly Ser Thr Thr Phe Asp
541 Gln Gly Phe Pro Ser Thr Met Ser Ala Asn Gly Ser Leu Thr Ser
556 Gln Ser Phe Arg Phe Ala Glu Phe Pro Val Gly Ile Ser Thr Ser
```

Figure 3B

```
571 Gly Ser Gln Thr Ala Gly Ile Ser Ile Ser Asn Asn Pro Gly Arg
586 Gln Thr Phe His Leu Asp Arg Ile Glu Phe Ile Pro Val Asp Ala
601 Thr Phe Glu Ala Glu Tyr Asp Leu Glu Arg Ala Gln Lys Ala Val
616 Asn Ser Leu Phe Thr Ser Ser Asn Gln Ile Glu Leu Lys Thr Asp
631 Val Thr Asp Tyr His Ile Asp Gln Val Ser Asn Leu Val Asp Cys
646 Leu Ser Asp Glu Phe Cys Leu Asp Glu Lys Arg Glu Leu Ser Glu
661 Lys Val Lys His Ala Lys Arg Leu Ser Asp Glu Arg Asn Leu Leu
676 Gln Asp Pro Asn Phe Arg Gly Ile Asn Arg Gln Pro Asp Arg Gly
691 Trp Arg Gly Ser Thr Asp Ile Thr Ile Gln Gly Gly Asp Asp Val
706 Phe Lys Glu Asn Tyr Val Thr Leu Pro Gly Thr Phe Asp Glu Cys
721 Tyr Pro Thr Tyr Leu Tyr Gln Lys Ile Asp Glu Ser Lys Leu Lys
736 Ala Tyr Asn Arg Tyr Gln Leu Arg Gly Tyr Ile Glu Asp Ser Gln
751 Asp Leu Glu Ile Tyr Leu Ile Arg Tyr Asn Ala Lys His Glu Thr
766 Val Asn Val Pro Gly Thr Gly Ser Leu Trp Pro Leu Ser Val Glu
781 Ser Pro Ile Gly Arg Cys Gly Glu Pro Asn Arg Cys Val Pro His
796 Leu Glu Trp Asn Pro Asp Leu Asp Cys Ser Cys Arg Asp Gly Glu
811 Lys Cys Ala His His Ser His Phe Ser Leu Asp Ile Asp Val
```

Figure 3C

```
826  Gly Cys Thr Asp Leu Gln Glu Asp Leu Gly Val Trp Val Val Phe
841  Lys Ile Lys Thr Gln Glu Gly Tyr Ala Arg Leu Gly Asn Leu Glu
856  Phe Ile Glu Glu Lys Pro Leu Ile Gly Glu Ala Leu Ser Arg Val
871  Lys Arg Ala Glu Lys Lys Trp Arg Asp Lys Arg Glu Lys Leu Gln
886  Leu Glu Thr Lys Arg Val Tyr Thr Glu Ala Lys Glu Ala Val Asp
901  Ala Leu Phe Val Asp Ser Gln Tyr Asp Arg Leu Gln Ala Asp Thr
916  Asn Ile Gly Met Ile His Ala Ala Asp Arg Leu Val His Gln Ile
931  His Glu Ala Tyr Leu Pro Glu Leu Pro Phe Ile Pro Gly Ile Asn
946  Val Val Ile Phe Glu Leu Glu Asn Arg Ile Ser Thr Ala Leu
961  Ser Leu Tyr Asp Ala Arg Asn Val Ile Lys Asn Gly Asp Phe Asn
976  Asn Gly Leu Ser Cys Trp Asn Val Lys Gly His Val Asp Val Val
991  Glu Gln Asn His Arg Ser Val Leu Val Pro Glu Trp Glu Trp Glu
1006 Ala Glu Val Ser Gln Thr Ile Arg Val Cys Pro Gly Arg Gly Tyr
1021 Ile Leu Arg Val Thr Ala Tyr Lys Glu Gly Tyr Gly Glu Gly Cys
1036 Val Thr Ile His Glu Ile Glu Asn Thr Asp Glu Leu Lys Phe
```

Figure 3D

```
1051 Lys Asn Cys Glu Glu Glu Val Tyr Pro Thr Asp Thr Gly Thr
1066 Cys Asn Asp Tyr Thr Ala His Gln Gly Thr Ala Gly Ser Thr Asp
1081 Ser Cys Asn Ser Arg Asn Ile Arg Tyr Glu Asp Ala Tyr Glu Met
1096 Asn Thr Thr Ala Ser Val Asn Tyr Lys Pro Thr Tyr Glu Glu Glu
1111 Arg Tyr Thr Asp Val Gln Gly Asp Asn His Cys Glu Tyr Asp Arg
1126 Gly Tyr Val Asn Tyr Arg Pro Val Pro Ala Gly Tyr Val Thr Lys
1141 Glu Leu Glu Tyr Phe Pro Glu Thr Asp Lys Val Trp Ile Glu Ile
1156 Gly Glu Thr Glu Gly Lys Phe Ile Val Asp Asn Val Glu Leu Leu
1171 Leu Met Glu Glu
```

Figure 3E

```
                                5              10              15             20
Met Glu Asn Asn Ile Glu Asn Gln Cys Ile Pro Tyr Asn Cys Leu Asn Asn Pro Glu Val
ATG GAG AAT AAT ATT GAA AAT CAA TGC ATA CCT TAC AAT TGT TTA AAT AAT CCT GAA GTA 25              30              35             40
Glu Ile Leu Gly Ile Glu Arg Ser Asn Ser Asn Val Ala Ala Glu Ile Gly Leu Gly Leu
GAG ATA TTA GGG ATT GAA AGG TCA AAT AGT AAC GTA GCA GCA GAA ATC GGC TTG GGG CTT 45              50              55             60
Ser Arg Leu Leu Val Ser Arg Ile Pro Leu Gly Asp Phe Ile Leu Gly Leu Phe Asp Val
AGT CGT CTG CTC GTT TCC CGA ATT CCA CTA GGG GAT TTT ATA CTT GGC TTG TTT GAT GTA 65              70              75             80
Ile Trp Gly Ala Ile Gly Pro Ser Gln Trp Asp Ile Phe Leu Glu Gln Ile Glu Leu Leu
ATA TGG GGG GCT ATA GGT CCT TCA CAA TGG GAT ATA TTT TTA GAG CAA ATT GAG CTA TTG 85              90              95            100
Ile Gly Gln Arg Ile Glu Glu Phe Ala Arg Asn Gln Ala Ile Ser Arg Leu Gln Gly Leu
ATC GGC CAA AGA ATA GAG GAA TTC GCT AGG AAT CAG GCA ATT TCT AGA TTA CAA GGG CTA
```

Figure 4A

```
                    105                          110                          115                         120
Ser Asn Leu Tyr Arg Ile Tyr Thr Asn Ala Phe Lys Asn Trp Glu Val Asp Pro Thr Asn
AGC AAT CTT TAC CGA ATT TAC ACA AAT GCT TTT AAA AAC TGG GAA GTA GAT CCT ACT AAT 125                          130                          135                         140
Pro Ala Leu Arg Glu Glu Met Arg Ile Gln Phe Asn Asp Met Asn Ser Ala Leu Thr Thr
CCA GCA TTA AGA GAA GAG ATG CGT ATT CAA TTT AAT GAC ATG AAC AGT GCT CTT ACA ACA 145                          150                          155                         160
Ala Ile Pro Leu Phe Ser Val Gln Gly Tyr Glu Ile Pro Leu Leu Ser Val Tyr Val Gln
GCT ATT CCT CTT TTT TCA GTT CAA GGT TAT GAA ATT CCT CTT TTA TCA GTA TAT GTT CAA 165                          170                          175                         180
Ala Ala Asn Leu His Leu Ser Val Leu Arg Asp Val Ser Val Phe Gly Gln Arg Trp Gly
GCT GCA AAT TTA CAT TTA TCG GTT TTG AGA GAT GTT TCA GTG TTT GGA CAA CGT TGG GGA 185                          190                          195                         200
Phe Asp Val Ala Thr Ile Asn Ser Arg Tyr Asn Asp Leu Thr Arg Leu Ile Gly Glu Tyr
TTT GAT GTA GCA ACA ATC AAT AGT CGT TAT AAT GAT TTA ACT AGG CTT ATT GGC GAA TAT
```

Figure 4B

```
                        205                     210                     215                     220
Thr Asp Tyr Ala Val Arg Trp Tyr Asn Thr Gly Leu Asn Arg Leu Pro Arg Asn Glu Gly
ACT GAT TAT GCT GTA CGT TGG TAT AAT ACG GGG TTA AAT CGT CCA AAT GAA GGG 225                     230                     235                     240
Val Arg Gly Trp Ala Arg Phe Asn Arg Arg Glu Leu Thr Ile Ser Val Leu Asp
GTA CGA GGA TGG GCA AGA TTT AAT AGG AGA GAG TTA ACA ATA TCA GTA TTA GAT 245                     250                     255                     260
Ile Ile Ser Phe Gln Asn Tyr Asp Ser Arg Leu Tyr Pro Thr Ile Tyr Gln
ATT ATT TCT TTT CAA AAT TAC GAT TCT AGA TTA TAT CCA ACA ATC TAT CAA 265                     270                     275                     280
Leu Thr Arg Glu Val Tyr Thr Asp Pro Val Ile Asn Ile Thr Asp Tyr Arg Val Thr Pro
TTA ACG CGG GAA GTA TAT ACA GAT CCG GTA ATT AAT ATA ACT GAT TAT AGA GTT ACC CCA
```

Figure 4C

```
              285                     290                     295                     300
Ser Phe Glu Ser Ile Glu Asn Ser Ala Ile Arg Ser Pro His Leu Met Asp Phe Leu Asn
AGT TTC GAG AGT ATT GAA AAT TCA GCT ATT AGA AGT CCC CAT CTT ATG GAT TTC TTA AAT 305                     310                     315                     320
Asn Ile Ile Ile Asp Thr Asp Leu Ile Arg Gly Val His Tyr Trp Ala Gly His Arg Val
AAT ATA ATT ATT GAC ACT GAT TTA ATT AGA GGC GTT CAC TAT TGG GCG GGG CAT CGT GTA 325                     330                     335                     340
Thr Ser His Phe Thr Gly Ser Ser Gln Val Ile Ser Ser Pro Gln Tyr Gly Ile Thr Ala
ACT TCT CAT TTT ACC GGT AGT TCG CAA GTG ATA AGC TCC CCT CAA TAC GGG ATA ACT GCA 345                     350                     355                     360
Asn Ala Glu Pro Ser Arg Thr Ile Ala Pro Ser Thr Phe Pro Gly Leu Asn Leu Phe Tyr
AAC GCA GAA CCG AGT CGA ACT ATT GCT CCT AGC ACT TTT CCA GGT CTT AAT CTA TTT TAT
```

Figure 4D

```
              365                 370             375                 380
Arg Thr Leu Ser Asp Pro Phe Phe Arg Arg Ser Asp Asn Ile Met Pro Thr Leu Gly Ile
AGA ACA CTA TCA GAC CCT TTC TTC CGA AGA TCC GAT AAT ATT ATG CCA ACA TTA GGA ATA 385                 390             395                 400
Asn Val Val Gln Gly Val Gly Phe Ile Gln Pro Asn Asn Gly Glu Val Leu Tyr Arg Arg
AAT GTA GTG CAG GGG GTA GGA TTC ATT CAA CCA AAT AAT GGT GAA GTT CTA TAT AGA AGG 405                 410             415                 420
Arg Gly Thr Val Asp Ser Leu Asp Glu Pro Ile Asp Gly Glu Asn Ser Leu Val Gly
AGA GGA ACA GTA GAT TCT CTT GAT GAG CCA ATT GAC GGT GAG AAT TCA TTA GTT GGA 425                 430             435                 440
Tyr Ser His Arg Leu Ser His Val Thr Leu Thr Arg Ser Leu Tyr Asn Thr Asn Ile Thr
TAT AGT CAT AGA TTA AGT CAC GTT ACA CTA ACC AGG TCG TTA TAT AAT ACT AAT ATA ACT 445                 450             455                 460
Ser Leu Pro Thr Phe Val Trp Thr His His Ser Ala Thr Asp Arg Asn Ile Ile Tyr Pro
AGC TTG CCA ACA TTT GTT TGG ACA CAT CAC AGT GCT ACT GAT CGA AAT ATA ATC TAT CCG
```

Figure 4E

```
        465                       470                       475                       480
Asp Val Ile Thr Gln Ile Pro Leu Val Lys Ser Phe Ser Leu Thr Ser Gly Thr Ser Val
GAT GTA ATT ACA CAA ATA CCA TTG GTA AAA TCA TTC TCC CTT ACT TCA GGT ACC TCT GTA 485                       490                       495                       500
Val Arg Gly Pro Gly Phe Thr Gly Gly Asp Ile Ile Arg Thr Asn Val Asn Gly Asn Val
GTC AGA GGC CCA GGA TTT ACA GGA GGG GAT ATC ATC CGA ACT AAC GTT AAT GGT AAT GTA 505                       510                       515                       520
Leu Ser Met Ser Leu Asn Phe Ser Asn Thr Ser Leu Gln Arg Tyr Arg Val Arg Val Arg
CTA AGT ATG AGT CTT AAT TTT AGT AAT ACA TCA TTA CAG CGG TAT CGC GTG AGA GTT CGT 525                       530                       535                       540
Tyr Ala Ala Ser Gln Thr Met Thr Met Val Met Arg Val Asn Val Gly Ser Thr Thr Phe Asp
TAT GCT GCT TCT CAA ACA ATG ACA ATG GTC ATG AGA GTA AAT GTT GGA GGG AGT ACT ACT TTT GAT 545                       550                       555                       560
Gln Gly Phe Pro Ser Thr Met Ser Ala Asn Gly Ser Leu Thr Ser Gln Ser Phe Arg Phe
CAA GGA TTC CCT AGT ACT ATG AGT GCA AAT GGG TCT TTG ACA TCT CAA TCA TTT AGA TTT 565                       570                       575                       580
Ala Glu Phe Pro Val Gly Ile Ser Thr Ser Gly Ser Gln Thr Ala Gly Ile Ser Ile Ser
GCA GAA TTT CCT GTA GGC ATT AGT ACT AGT GGC AGT CAA ACT GCT GGA ATA AGT ATA AGT
```

Figure 4F

```
              585                 590                 595             600
Asn Asn Pro Gly Arg Gln Thr Phe His Leu Asp Arg Ile Glu Phe Ile Pro Val Asp Ala
AAT AAT CCA GGT AGA CAA ACG TTT CAC TTA GAT AGA ATT GAA TTT ATC CCA GTT GAT GCA 605                 610                 615             620
Thr Phe Glu Ala Glu Tyr Asp Leu Glu Arg Ala Gln Lys Ala Val Asn Ser Leu Phe Thr
ACA TTT GAA GCA GAA TAT GAT TTA GAA AGA GCA CAA AAG GCG GTG AAT TCG CTG TTT ACT 625                 630                 635             640
Ser Ser Asn Gln Ile Glu Leu Lys Thr Asp Val Thr Asp Tyr His Ile Asp Gln Val Ser
TCT TCC AAT CAA ATC GAG TTA AAA ACA GAT GTG ACG GAT TAT CAT ATT GAT CAA GTA TCC 645                 650                 655             660
Asn Leu Val Asp Cys Leu Ser Asp Glu Phe Cys Leu Asp Glu Lys Arg Glu Leu Ser Glu
AAT TTA GTA GAT TGT TTA TCC GAT GAA TTT TGT CTG GAT GAA AAG CGA GAA TTG TCC GAG 665                 670                 675             680
Lys Val Lys His Ala Lys Arg Leu Ser Asp Glu Arg Asn Leu Leu Gln Asp Pro Asn Phe
AAA GTC AAA CAT GCG AAG CGA CTC AGT GAT GAG CGG AAT TTA CTT CAA GAT CCA AAC TTC
```

Figure 4G

```
                                685                690                695                700
Arg Gly Ile Asn Arg Gln Pro Asp Arg Gly Trp Arg Gly Ser Thr Asp Ile Thr Ile Gln
AGA GGG ATC AAT AGG CAA CCA GAC CGT GGC TGG AGA GGA AGT ACG GAT ATT ACC ATC CAA 705                710                715                720
Gly Gly Asp Asp Val Phe Lys Glu Asn Tyr Val Thr Leu Pro Gly Thr Phe Asp Glu Cys
GGA GGA GAT GAC GTA TTC AAA GAG AAT TAC GTC ACA CTA CCA GGT ACC TTT GAT GAG TGC 725                730                735                740
Tyr Pro Thr Tyr Leu Tyr Gln Lys Ile Asp Glu Ser Lys Leu Lys Ala Tyr Asn Arg Tyr
TAT CCA ACG TAT TTG TAT CAA AAA ATA GAT GAG TCG AAA TTA AAA GCC TAT AAC CGT TAC 745                750                755                760
Gln Leu Arg Gly Tyr Ile Glu Asp Ser Gln Asp Leu Glu Ile Tyr Leu Ile Arg Tyr Asn
CAA TTA AGA GGG TAT ATC GAA GAT AGT CAA GAC TTA GAA ATC TAT TTA ATT CGC TAC AAT 765                770                775                780
Ala Lys His Glu Thr Val Asn Val Pro Gly Thr Gly Ser Leu Trp Pro Leu Ser Val Glu
GCA AAA CAC GAA ACA GTA AAT GTA CCA GGT ACG GGT TCC CTT TGG CCG CTT TCA GTC GAA
```

Figure 4H

```
                785                    790                    795                    800
Ser Pro Ile Gly Arg Cys Gly Glu Pro Asn Arg Cys Val Pro His Leu Glu Trp Asn Pro
AGT CCA ATT GGA AGG TGT GGA GAA CCG AAT CGG TGT GTG CCA CAC CTT GAA TGG AAT CCT 805                    810                    815                    820
Asp Leu Asp Cys Ser Cys Arg Asp Gly Glu Lys Cys Ala His Ser His His Phe Ser
GAT TTA GAT TGT TCC TGC AGA GAC GGG GAA AAA TGT GCA CAT TCC CAT CAT TTC TCC 825                    830                    835                    840
Leu Asp Ile Asp Val Gly Cys Thr Asp Leu Gln Glu Asp Leu Gly Val Trp Val Val Phe
TTG GAC ATT GAT GTT GGA TGC ACA GAC TTG CAA GAG GAT CTA GGC GTG TGG GTT GTA TTC 845                    850                    855                    860
Lys Ile Lys Thr Gln Glu Gly Tyr Ala Arg Leu Gly Asn Leu Glu Phe Ile Glu Glu Lys
AAG ATT AAG ACG CAG GAA GGT TAT GCA AGA TTA GGA AAT CTG GAA TTT ATC GAA GAG AAA 865                    870                    875                    880
Pro Leu Ile Gly Glu Ala Leu Ser Arg Val Lys Arg Ala Glu Lys Lys Trp Arg Asp Lys
CCA TTA ATT GGA GAA GCA CTG TCT CGT GTG AAG AGA GCG GAA AAA AAA TGG AGA GAC AAA
```

Figure 4I

```
                                    885                        890                        895                        900
Arg Glu Lys Leu Gln Leu Glu Thr Lys Arg Val Tyr Thr Glu Ala Lys Glu Ala Val Asp
CGG GAA AAA CTA CAA TTG GAA ACA AAA CGA GTA TAT ACA GAG GCA AAA GAA GCT GTG GAT 905                        910                        915                        920
Ala Leu Phe Val Asp Ser Gln Tyr Asp Arg Leu Gln Ala Asp Thr Asn Ile Gly Met Ile
GCT TTA TTC GTA GAT TCT CAA TAT GAT AGA TTA CAA GCA GAT ACA AAC ATT GGT ATG ATT 925                        930                        935                        940
His Ala Ala Asp Arg Leu Val His Gln Ile His Glu Ala Tyr Leu Pro Glu Leu Pro Phe
CAT GCG GCA GAT AGA CTT GTT CAT CAG ATC CAC GAG GCT TAT CTT CCA GAA CTA CCT TTC 945                        950                        955                        960
Ile Pro Gly Ile Asn Val Val Ile Phe Glu Glu Leu Glu Asn Arg Ile Ser Thr Ala Leu
ATT CCA GGA ATA AAT GTG GTG ATT TTT GAA GAA TTA GAA AAC CGT ATT TCT ACT GCA TTA 965                        970                        975                        980
Ser Leu Tyr Asp Ala Arg Asn Val Ile Lys Asn Gly Asp Phe Asn Asn Gly Leu Ser Cys
TCC CTA TAT GAT GCG AGA AAT GTC ATT AAA AAT GGC GAT TTC AAT AAT GGC TTA TCA TGC
```

Figure 4J

```
                                985                         990                              995                              1000
Trp Asn Val Lys Gly His Val Asp Val Val Glu Gln Asn Asn His Arg Ser Val Leu Val
TGG AAC GTG AAA GGG CAT GTA GAT GTA GAA CAA AAC CAC CGT TCG GTC CTT GTT 1005                        1010                             1015                             1020
Val Pro Glu Trp Glu Ala Glu Val Ser Gln Thr Ile Arg Val Cys Pro Gly Arg Gly Tyr
GTC CCG GAA TGG GAA GCA GAA GTG TCA CAA ACA ATT CGT GTC TGT CCG GGG CGT TAT 1025                        1030                             1035                             1040
Ile Leu Arg Val Thr Ala Tyr Lys Glu Gly Tyr Gly Glu Gly Cys Val Thr Ile His Glu
ATC CTC CGT GTT ACA GCG TAC AAA GAG GGA TAT GGA GAA GGT TGC GTA ACC ATC CAT GAG 1045                        1050                             1055                             1060
Ile Glu Asn Asn Thr Asp Glu Leu Lys Phe Lys Asn Cys Glu Glu Glu Val Tyr Pro
ATC GAG AAC AAT ACA GAC GAA CTA AAA TTT AAA AAC TGT GAA GAA GAG GAA GTG TAT CCA 1065                        1070                             1075                             1080
Thr Asp Thr Gly Thr Cys Asn Asp Tyr Thr Ala His Gln Gly Thr Ala Gly Ser Thr Asp
ACG GAT ACA GGA ACG TGT AAT GAT TAT ACT GCA CAC CAA GGT ACA GCA GGA TCC ACA GAT
```

Figure 4K

```
        1085                    1090                    1095                    1100
Ser Cys Asn Ser Arg Asn Ile Arg Tyr Glu Asp Ala Tyr Glu Met Asn Thr Thr Ala Ser
TCA TGT AAT TCC CGT AAT ATC AGA TAT GAG GAT GCA TAT GAA ATG AAT ACT ACA GCA TCT 1105                    1110                    1115                    1120
Val Asn Tyr Lys Pro Thr Tyr Glu Glu Arg Tyr Thr Asp Val Gln Gly Asp Asn His
GTT AAT TAC AAA CCG ACT TAC GAA GAA AGG TAT ACA GAT GTA CAA GGA GAT AAT CAT 1125                    1130                    1135                    1140
Cys Glu Tyr Asp Arg Gly Tyr Val Asn Tyr Arg Pro Val Pro Ala Gly Tyr Val Thr Lys
TGT GAA TAT GAC AGA GGG TAT GTG AAT TAT CGA CCA GTA CCA GCT GGT TAT GTG ACA AAA 1145                    1150                    1155                    1160
Glu Leu Glu Tyr Phe Pro Glu Thr Asp Lys Val Trp Ile Glu Ile Gly Glu Thr Glu Gly
GAA TTA GAG TAC TTC CCA GAA ACC GAT AAG GTA TGG ATT GAG ATC GGA GAA ACG GAA GGG 1165                    1170
Lys Phe Ile Val Asp Asn Val Glu Leu Leu Met Glu Glu
AAG TTT ATT GTA GAC AAT GTC GAA TTA CTC CTT ATG GAG GAA
```

Figure 4L

```
            10         20         30         40         50         60
  1 ATGGAGATAA TGAATAATCA GAATCAATGC GTTCCTTATA ACTGTTTGAA TGATCCGACA
 61 ATTGAAATAT TAGAAGGAGA AAGAATAGAA ACTGGTTACA CCCCAATAGA TATTTCCTTG
121 TCGCTAACGC AATTTCTGTT GAGTGAATTT GTCCCAGGTG CTGGGTTTGT ATTAGGTTTA
181 ATTGATTTAA TATGGGGGTT TGTGGGTCCC TCTCAATGGG ATGCATTTCT TGTGCAAATT
241 GAACAGTTAA TTAACCAAAG AATAGAGGAA TTCGCTAGGA ACCAAGCAAT TTCTAGATTA 310        320        330        340        350        360
301 GAAGGGCTAA GCAACCTTTA TCAAATTTAC GCAGAAGCTT TTAGAGAGTG GGAAGCAGAT
361 CCTACTAATC CAGCATTAAC AGAAGAGATG CGTATTCAGT TCAATGACAT GAACAGTGCT
421 CTTACAACCG CTATTCCTCT TTTTACAGTT CAAAATTATC AAGTACCTCT TCTATCAGTA
481 TATGTTCAAG CTGCAAATTT ACATTATCG GTTTTGAGAG ATGTTTCAGT GTTGGACAA
541 CGTTGGGGAT TTGATGTAGC AACAATCAAT AGTCGTTATA ATGATTTAAC TAGGCTTATT 610        620        630        640        650        660
601 GGCACCCTATA CAGATTATGC TGTACGCTGG TATAATACGG GATTAGAACG TGTATGGGGA
661 CCGGATTCTA GAGATTGGGT AAGTATATAAT CAATTTAGAA GAGAGCTAAC ACTAACTGTA
721 TTAGATATCG TTTCTCTGTT CCCGAACTAT GATAGTAGAA CGTATCCAAT TCGAACAGTT
781 TCCCAATTAA CTAGAGAAAT TTATACAAAC CCAGTATTAG AAAATTTTGA TGGTAGTTTT
841 CGTGGAATGG CTCAGAGAAT AGAACAGAAT ATTAGGCAAC CACATCTTAT GGATCTCCTT
```

Figure 5A

```
     910         920         930         940         950         960
901  AATAGTATAA CCATTTATAC TGATGTGCAT AGAGGCTTTA ATTATTGGTC AGGACATCAA
961  ATAACAGCTT CTCCTGTCGG TTTTGCGGGG CCAGAATTTA CTTTTCCTAG ATATGGAACC
1021 ATGGGAAATG CTGCTCCACC CGTACTGATC TCAACTACTG GTTTGGGGAT TTTTAGAACA
1081 TTATCTTCAC CTCTTTACAG AAGAATTATA CTTGGTTCAG GCCCAAATAA TCAGAACCTG
1141 TTTGTCCTTG ATGGAACGGA ATTTCTTTT GCCTCCCTAA CAGCCGATTT ACCTTCTACT 1210        1220        1230        1240        1250        1260
1201 ATATACAGAC AAAGGGGAAC GGTCGATTCA CTAGATGTAA TACCGCCACA GGATAATAGT
1261 GTGCCAGCAC GTGCGGGATT TAGTCATCATG TTAAGTCATG TTACAATGCT GAGCCAAGCA
1321 GCTGGAGCAC TTTACACCTT GAGAGCTCCA ACGTTTTCTT GGCGACATCG TAGTGCTGAA
1381 TTCTCTAACC TAATTCCTTC ATCACAAATC ACACAGATAC CTTTAACAAA GTCTATTAAT
1441 CTTGGCTCTG GGACCTCTGT TGTTAAAGGA CCAGGATTTA CAGGAGGAGA TATTCTTCGA 1510        1520        1530        1540        1550        1560
1501 AGAACTTCAC CTGGCCAGAT TTCAACCTTA AGAGTGACTA TTACTGCACC ATTATCACAA
1561 AGATATCGCG TAAGAATTCG CTACGCTTCT ACTACAAATT TACAATTCCA TACATCAATT
1621 GACGGAAGAC CTATTAATCA GGGGAATTTT TCAGCAACTA TGAGTAGTGG GGGTAATTTA
1681 CAGTCCGGAA GCTTTAGGAC TGCAGGTTTT ACTACTCCGT TTAACTTTTC AAATGGATCA
1741 AGTATATTTA CGTTAAGTGC TCATGTCTTC AATTCAGGCA ATGAAGTTTA TATAGATCGA
```

Figure 5B

```
          1810       1820       1830       1840       1850       1860
1801 ATTGAATTTG TTCCGGCAGA AGTAACATTT GAGGCGGAAT ATGATTTAGA AAGAGCGCAA
1861 GAGGCGGTGA ATGCTCTGTT TACTTCTTCC AATCAACTAG GATTAAAAAC AAATGTGACG
1921 GACTATCATA TTGATCAAGT GTCCAATCTA GTCGAATGTT TATCCGGTGA ATTCTGTCTG
1981 GATGAAAAGA GAGAATTGTC CGAGAAAGTC AAACATGCGA AGCGACTCAG TGATGAGCGG
2041 AATTTACTTC AAGACCCAAA CTTCAGAGGC ATCAATAGAC AACCAGACCG TGGCTGGAGA 2110       2120       2130       2140       2150       2160
2101 GGCAGTACGG ATATTACCAT CCAAGGAGGA GATGACGTAT TCAAAGAGAA TTACGTCACA
2161 CTACCGGGTA CCTTTAATGA GTGTTATCCT ACGTATCTGT ATCAAAAAT AGATGAGTCG
2221 AAATTAAAAG CCTATACCCG TTACCAATTA AGAGGGTACA TCGAGGATAG TCAAGACTTA
2281 GAAATCTATT TAATTCGCTA CAATACAAAA CACGAAAACAG TAAATGTGCC AGGTACGGGT
2341 TCCTTATGGC CGCTTTCAGT CGAAAATCCA ATTGGAAAGT GCGGAGAACC AAATCGATGC
```

Figure 5C

```
           2410       2420       2430       2440       2450       2460
2401 GCACCACAAC TTGAATGGAA TCCTGATCTA GATTGTTCCT GCAGAGACGG GGAAAAATGT
2461 GCACATCACT CCCATCATTT CTCCTTGGAC ATTGATATTG GATGTACAGA TTTAAATGAG
2521 AACTTAGGTG TATGGGTGAT ATTCAAAATT AAGACGCAAG ATGGTCACGC AAGACTAGGT
2581 AATCTAGAGT TTCTCGAAGA GAAACCATTA GTAGGCGAAT CGTTAGCACG CGTGAAGAGA
2641 GCGGAGAAGA AGTGGAGAGA CAAACGAGAG AAATTGCAAG TGGAAACAAA TATCGTTTAT 2710       2720       2730       2740       2750       2760
2701 AAAGAGGCAA AAGAATCTGT AGATGCTTTA TTTGTGAACT CTCAATATGA TAGATTACAA
2761 GCGGATACCG ACATCGCGAT GATTCATGCG GCAGATAAAC GCGTTCATCG AATTCGAGAA
2821 GCATATCTTC CAGAGTTATC TGTAATTCCG GGTGTCAATG CGGGCATTTT TGAAGAATTA
2881 GAGGGACGTA TTTTCACAGC CTACTCTTTA TATGATGCGA GAAATGTCAT TAAAAATGGC
2941 GATTTCAATA ATGGCTTATC ATGCTGGAAC GTGAAAGGGC ATGTAGATGT AGAAGAACAA
```

Figure 5D

```
           3010       3020       3030       3040       3050       3060
3001 AACAACCACC GTTCGGTTCT TGTTGTCCCG GAATGGGAAG CAGAGGTGTC ACAAGAGGTT
3061 CGTGTCTGTC CAGGTCGTGG CTATATCCTA CGTGTTACAG CGTACAAAGA GGGATATGGA
3121 GAAGGTTGCG TAACGATTCA TGAGATCGAA GACAATACAG ACGAACTGAA ATTCAGCAAC
3181 TGTGTAGAAG AGGAAGTATA TCCAAACAAC ACGGTAACGT GTAATGATTA TACTGCAAAT
3241 CAAGAAGAAT ACGGGGGTGC GTACACTTCT CGTAATCGTG GATATGGTGA ATCTTATGAA 3310       3320       3330       3340       3350       3360
3301 AGTAATTCTT CCATACCAGC TGAGTATGCG CCAGTTTATG AGGAAGCATA TATAGATGGA
3361 AGAAAGAGA ATCCTTGTGA ATCTAACAGA GGATATGGGG ATTACACGCC ACTACCAGCT
3421 GGTTATGTGA CAAAGAATT AGAGTACTTC CCAGAAACCG ATAAGGTATG GATTGAGATC
3481 GGGGAAACGG AAGGAACATT CATCGTGGAT AGCGTGGAAT TACTCCTTAT GGAGGAA*
```

Segment 1-*

Figure 5E

```
                          5                   10                  15
  1 Met Glu Ile Met Asn Asn Gln Asn Cys Val Pro Tyr Asn Cys
 16 Leu Asn Asp Pro Thr Ile Glu Ile Leu Glu Gly Glu Arg Ile Glu
 31 Thr Gly Tyr Thr Pro Ile Asp Ile Ser Leu Ser Leu Thr Gln Phe
 46 Leu Leu Ser Glu Phe Val Pro Gly Ala Gly Phe Val Leu Gly Leu
 61 Ile Asp Leu Ile Trp Gly Phe Val Gly Pro Ser Gln Trp Asp Ala
 76 Phe Leu Val Gln Ile Glu Gln Leu Ile Asn Gln Arg Ile Glu Glu
 91 Phe Ala Arg Asn Gln Ala Ile Ser Arg Leu Glu Gly Leu Ser Asn
106 Leu Tyr Gln Ile Tyr Ala Glu Ala Phe Arg Glu Trp Glu Ala Asp
121 Pro Thr Asn Pro Ala Leu Thr Glu Glu Met Arg Ile Gln Phe Asn
136 Asp Met Asn Ser Ala Leu Thr Thr Ala Ile Pro Leu Phe Thr Val
151 Gln Asn Tyr Gln Val Pro Leu Leu Ser Val Tyr Val Gln Ala Ala
166 Asn Leu His Leu Ser Val Leu Arg Asp Val Ser Val Phe Gly Gln
181 Arg Trp Gly Phe Asp Val Ala Thr Ile Asn Ser Arg Tyr Asn Asp
196 Leu Thr Arg Leu Ile Gly Thr Tyr Thr Asp Tyr Ala Val Arg Trp
```

Figure 6A

211 Tyr Asn Thr Gly Leu Glu Arg Val Trp Gly Pro Asp Ser Arg Asp
226 Trp Val Arg Tyr Asn Gln Phe Arg Arg Glu Leu Thr Leu Thr Val
241 Leu Asp Ile Val Ser Leu Phe Pro Asn Tyr Asp Ser Arg Thr Tyr
256 Pro Ile Arg Thr Val Ser Gln Leu Thr Arg Glu Ile Tyr Thr Asn
271 Pro Val Leu Glu Asn Phe Asp Gly Ser Phe Arg Gly Met Ala Gln
286 Arg Ile Glu Gln Asn Ile Arg Gln Pro His Leu Met Asp Leu Leu
301 Asn Ser Ile Thr Ile Tyr Thr Asp Val His Arg Gly Phe Asn Tyr
316 Trp Ser Gly His Gln Ile Thr Ala Ser Pro Val Gly Phe Ala Gly
331 Pro Glu Phe Thr Phe Pro Arg Tyr Gly Thr Met Gly Asn Ala Ala
346 Pro Pro Val Leu Ile Ser Thr Thr Gly Leu Gly Ile Phe Arg Thr
361 Leu Ser Ser Pro Leu Tyr Arg Arg Ile Ile Leu Gly Ser Gly Pro
376 Asn Asn Gln Asn Leu Phe Val Leu Asp Gly Thr Glu Phe Ser Phe
391 Ala Ser Leu Thr Ala Asp Leu Pro Ser Thr Ile Tyr Arg Gln Arg
406 Gly Thr Val Asp Ser Leu Asp Val Ile Pro Pro Gln Asp Asn Ser
421 Val Pro Ala Arg Ala Gly Phe Ser His Arg Leu Ser His Val Thr
436 Met Leu Ser Gln Ala Gly Ala Val Tyr Thr Leu Arg Ala Pro

Figure 6B

```
451 Thr Phe Ser Trp Arg His Arg Ser Ala Glu Phe Ser Asn Leu Ile
466 Pro Ser Ser Gln Ile Thr Gln Ile Pro Leu Thr Lys Ser Ile Asn
481 Leu Gly Ser Gly Thr Ser Val Val Lys Gly Pro Gly Phe Thr Gly
496 Gly Asp Ile Leu Arg Arg Thr Ser Pro Gly Gln Ile Ser Thr Leu
511 Arg Val Thr Ile Thr Ala Pro Leu Ser Gln Arg Tyr Arg Val Arg
526 Ile Arg Tyr Ala Ser Thr Thr Asn Leu Gln Phe His Thr Ser Ile
541 Asp Gly Arg Pro Ile Asn Gln Gly Asn Phe Ser Ala Thr Met Ser
556 Ser Gly Gly Asn Leu Gln Ser Gly Ser Phe Arg Thr Ala Gly Phe
571 Thr Thr Pro Phe Asn Phe Ser Asn Gly Ser Ser Ile Phe Thr Leu
586 Ser Ala His Val Phe Asn Ser Gly Asn Glu Val Tyr Ile Asp Arg
601 Ile Glu Phe Val Pro Ala Glu Val Thr Phe Glu Ala Glu Tyr Asp
616 Leu Glu Arg Ala Gln Glu Ala Val Asn Ala Leu Phe Thr Ser Ser
631 Asn Gln Leu Gly Leu Lys Thr Asn Val Thr Asp Tyr His Ile Asp
```

Figure 6C

```
646 Gln Val Ser Asn Leu Val Glu Cys Leu Ser Gly Glu Phe Cys Leu
661 Asp Glu Lys Arg Glu Leu Ser Glu Lys Val Lys His Ala Lys Arg
676 Leu Ser Asp Glu Arg Gly Asn Leu Gln Asp Pro Asn Phe Arg Gly
691 Ile Asn Arg Gln Pro Asp Arg Gly Trp Arg Gly Ser Thr Asp Ile
706 Thr Ile Gln Gly Gly Asp Val Phe Lys Glu Asn Tyr Val Thr
721 Leu Pro Gly Thr Phe Asn Glu Cys Tyr Pro Thr Tyr Leu Tyr Gln
736 Lys Ile Asp Glu Ser Lys Leu Lys Ala Tyr Thr Arg Tyr Gln Leu
751 Arg Gly Tyr Ile Glu Asp Ser Gln Asp Leu Glu Ile Tyr Leu Ile
766 Arg Tyr Asn Thr Lys His Glu Thr Val Asn Val Pro Gly Thr Gly
781 Ser Leu Trp Pro Leu Ser Val Glu Asn Pro Ile Gly Lys Cys Gly
796 Glu Pro Asn Arg Cys Ala Pro Gln Leu Glu Trp Asn Pro Asp Leu
811 Asp Cys Ser Cys Arg Asp Gly Glu Lys Cys Ala His His Ser His
```

Figure 6D

```
826  His Phe Ser Leu Asp Ile Asp Ile Gly Cys Thr Asp Leu Asn Glu
841  Asn Leu Gly Val Trp Val Ile Phe Lys Ile Lys Thr Gln Asp Gly
856  His Ala Arg Leu Gly Asn Leu Glu Phe Leu Glu Glu Lys Pro Leu
871  Val Gly Glu Ser Leu Ala Arg Val Lys Arg Ala Glu Lys Lys Trp
886  Arg Asp Lys Arg Glu Lys Leu Gln Val Glu Thr Asn Ile Val Tyr
901  Lys Glu Ala Lys Glu Ser Val Asp Ala Leu Phe Val Asn Ser Gln
916  Tyr Asp Arg Leu Gln Ala Asp Thr Asp Ile Ala Met Ile His Ala
931  Ala Asp Lys Arg Val His Arg Ile Arg Glu Ala Tyr Leu Pro Glu
946  Leu Ser Val Ile Pro Gly Val Asn Ala Gly Ile Phe Glu Glu Leu
961  Glu Gly Arg Ile Phe Thr Ala Tyr Ser Leu Tyr Asp Ala Arg Asn
976  Val Ile Lys Asn Gly Asp Phe Asn Asn Gly Leu Ser Cys Trp Asn
991  Val Lys Gly His Val Asp Val Glu Glu Gln Asn Asn His Arg Ser
1006 Val Leu Val Val Pro Glu Trp Glu Ala Glu Val Ser Gln Glu Val
```

Figure 6E

```
1021 Arg Val Cys Pro Gly Arg Gly Tyr Ile Leu Arg Val Thr Ala Tyr
1036 Lys Glu Gly Tyr Gly Glu Gly Cys Val Thr Ile His Glu Ile Glu
1051 Asp Asn Thr Asp Glu Leu Lys Phe Ser Asn Cys Val Glu Glu Glu
1066 Val Tyr Pro Asn Asn Thr Val Thr Cys Asn Asp Tyr Thr Ala Asn
1081 Gln Glu Glu Tyr Gly Ala Tyr Thr Ser Arg Asn Arg Gly Tyr
1096 Gly Glu Ser Tyr Glu Ser Asn Ser Ile Pro Ala Glu Tyr Ala
1111 Pro Val Tyr Glu Glu Ala Tyr Ile Asp Gly Arg Lys Glu Asn Pro
1126 Cys Glu Ser Asn Arg Gly Tyr Gly Asp Tyr Thr Pro Leu Pro Ala
1141 Gly Tyr Val Thr Lys Glu Leu Glu Tyr Phe Pro Glu Thr Asp Lys
1156 Val Trp Ile Glu Ile Gly Glu Thr Glu Gly Thr Phe Ile Val Asp
1171 Ser Val Glu Leu Leu Leu Met Glu Glu
```

Fragment 1-*

Figure 6F

```
         5                    10                   15                   20
Met Glu Ile Met Asn Asn Gln Asn Cys Val Pro Tyr Asn Cys Leu Asn Asp Pro Thr
ATG GAG ATA ATG AAT AAT CAG AAT TGC GTT CCT TAT AAC TGT TTG AAT GAT CCG ACA 25                   30                   35                   40
Ile Glu Ile Leu Glu Gly Glu Arg Ile Glu Thr Gly Tyr Thr Pro Ile Asp Ile Ser Leu
ATT GAA ATA TTA GAA GGA GAA AGA ATA GAA ACT GGT TAC ACC CCA ATA GAT ATT TCC TTG 45                   50                   55                   60
Ser Leu Thr Gln Phe Leu Leu Ser Glu Phe Val Pro Gly Ala Gly Phe Val Leu Gly Leu
TCG CTA ACG CAA TTT CTG TTG AGT GAA TTT GTC CCA GGT GCT GGG TTT GTA TTA GGT TTA 65                   70                   75                   80
Ile Asp Leu Ile Trp Gly Phe Val Gly Pro Ser Gln Trp Asp Ala Phe Leu Val Gln Ile
ATT GAT TTA ATA TGG GGG TTT GTG GGT CCC TCT CAA TGG GAT GCA TTT CTT GTG CAA ATT 85                   90                   95                   100
Glu Gln Leu Ile Asn Gln Arg Ile Glu Glu Phe Ala Arg Asn Gln Ala Ile Ser Arg Leu
GAA CAG TTA ATT AAC CAA AGA ATA GAG GAG TTC GCT AGG AAC CAA GCA ATT TCT AGA TTA
```

Figure 7A

```
         105                 110                 115                 120
Glu Gly Leu Ser Asn Leu Tyr Gln Ile Tyr Ala Glu Ala Phe Arg Glu Trp Glu Ala Asp
GAA GGG CTA AGC AAC CTT TAT CAA ATT TAC GCA GAA GCT TTT AGA GAG TGG GAA GCA GAT 125                 130                 135                 140
Pro Thr Asn Pro Ala Leu Thr Glu Glu Met Arg Ile Gln Phe Asn Asp Met Asn Ser Ala
CCT ACT AAT CCA GCA TTA ACA GAA GAG ATG CGT ATT CAG TTC AAT GAC ATG AAC AGT GCT 145                 150                 155                 160
Leu Thr Thr Ala Ile Pro Leu Phe Thr Val Gln Asn Tyr Gln Val Pro Leu Leu Ser Val
CTT ACA ACC GCT ATT CCT CTT TTT ACA GTT CAA AAT TAT CAA GTA CCT CTT CTA TCA GTA 165                 170                 175                 180
Tyr Val Gln Ala Ala Asn Leu His Leu Ser Val Leu Arg Asp Val Ser Val Phe Gly Gln
TAT GTT CAA GCT GCA AAT TTA CAT TTA TCG GTT TTG AGA GAT GTT TCA GTG TTT GGA CAA 185                 190                 195                 200
Arg Trp Gly Phe Asp Val Ala Thr Ile Asn Ser Arg Tyr Asn Asp Leu Thr Arg Leu Ile
CGT TGG GGA TTT GAT GTA GCA ACA ATC AAT AGT CGT TAT AAT GAT TTA ACT AGG CTT ATT
```

Figure 7B

```
                205                 210                 215             220
Gly Thr Tyr Thr Asp Tyr Ala Val Arg Trp Tyr Asn Thr Gly Leu Glu Arg Val Trp Gly
GGC ACC TAT ACA GAT TAT GCT GTA CGC TGG TAT AAT ACG GGA TTA GAA CGT GTA TGG GGA 225                 230                 235             240
Pro Asp Ser Arg Asp Trp Val Arg Tyr Asn Gln Phe Arg Arg Glu Leu Thr Leu Thr Val
CCG GAT TCT AGA GAT TGG GTA AGG TAT AAT CAA TTT AGA AGA GAG CTA ACA CTA ACT GTA 245                 250                 255             260
Leu Asp Ile Val Ser Leu Phe Pro Asn Tyr Asp Ser Arg Thr Tyr Pro Ile Arg Thr Val
TTA GAT ATC GTT TCT CTG TTC CCG AAC TAT GAT AGT AGA ACG TAT CCA ATT CGA ACA GTT 265                 270                 275             280
Ser Gln Leu Thr Arg Glu Ile Tyr Thr Asn Pro Val Leu Glu Asn Phe Asp Gly Ser Phe
TCC CAA TTA ACT AGA GAA ATT TAT ACA AAC CCA GTA TTA GAA AAT TTT GAT GGT AGT TTT
```

Figure 7C

```
                                        285                   290                   295                   300
            Arg Gly Met Ala Gln Arg Ile Glu Gln Asn Ile Arg Gln Pro His Leu Met Asp Leu Leu
            CGT GGA ATG GCT CAG AGA ATA GAA CAG AAT ATT AGG CAA CCA CAT CTT ATG GAT CTC CTT 305                   310                   315                   320
            Asn Ser Ile Thr Ile Tyr Thr Asp Val His Arg Gly Phe Asn Tyr Trp Ser Gly His Gln
            AAT AGT ATA ACC ATT TAT ACT GAT GTG CAT AGA GGC TTT AAT TAT TGG TCA GGA CAT CAA 325                   330                   335                   340
            Ile Thr Ala Ser Pro Val Gly Phe Ala Gly Pro Glu Phe Thr Phe Pro Arg Tyr Gly Thr
            ATA ACA GCT TCT CCT GTC GGT TTT GCG GGG CCA GAA TTT ACT TTT CCT AGA TAT GGA ACC 345                   350                   355                   360
            Met Gly Asn Ala Ala Pro Pro Val Leu Ile Ser Thr Thr Gly Leu Gly Ile Phe Arg Thr
            ATG GGA AAT GCT GCT CCA CCC GTA CTG ATC TCA ACT ACT GGT TTG GGG ATT TTT AGA ACA 365                   370                   375                   380
            Leu Ser Ser Pro Leu Tyr Arg Arg Ile Ile Leu Gly Ser Gly Pro Asn Asn Gln Asn Leu
            TTA TCT TCA CCT CTT TAC AGA AGA ATT ATA CTT GGT TCA GGC CCA AAT AAT CAG AAC CTG
```

Figure 7D

```
                                385                    390                    395             400
            Phe Val Leu Asp Gly Thr Glu Phe Ser Phe Ala Ser Leu Thr Ala Asp Leu Pro Ser Thr
            TTT GTC CTT GAT GGA ACG GAA TTT TCT TTT GCC TCC CTA ACA GCC GAT TTA CCT TCT ACT 405                    410                    415             420
            Ile Tyr Arg Gln Arg Gly Thr Val Asp Ser Leu Asp Val Ile Pro Pro Gln Asp Asn Ser
            ATA TAC AGA CAA AGG GGA ACG GTC GAT TCA CTA GAT GTA ATA CCG CCA CAG GAT AAT AGT 425                    430                    435             440
            Val Pro Ala Arg Ala Gly Phe Ser His Arg Leu Ser His Val Thr Met Leu Ser Gln Ala
            GTG CCA GCA CGT GCG GGA TTT AGT CAT CGA TTA AGT CAT GTT ACA ATG CTG AGC CAA GCA 445                    450                    455             460
            Ala Gly Ala Val Tyr Thr Leu Arg Ala Pro Thr Phe Ser Trp Arg His Arg Ser Ala Glu
            GCT GGA GCA GTT TAC ACC TTG AGA GCT CCA ACG TTT TCT TGG CGA CAT CGT AGT GCT GAA 465                    470                    475             480
            Phe Ser Asn Leu Ile Pro Ser Ser Gln Ile Thr Gln Ile Pro Leu Thr Lys Ser Ile Asn
            TTC TCT AAC CTA ATT CCT TCA TCA CAA ATC ACA CAG ATA CCT TTA ACA AAG TCT ATT AAT
```

Figure 7E

```
                          485                490                   495              500
          Leu Gly Ser Gly Thr Ser Val Val Lys Gly Pro Gly Phe Thr Gly Gly Asp Ile Leu Arg
          CTT GGC TCT GGG ACC TCT GTT AAA GGA CCA GGA TTT ACA GGA GGA GAT ATT CTT CGA 505                510                   515              520
          Arg Thr Ser Pro Gly Gln Ile Ser Thr Leu Arg Val Thr Ile Thr Ala Pro Leu Ser Gln
          AGA ACT TCA CCT GGC CAG ATT TCA ACC TTA AGA GTG ACT ATT ACT GCA CCA TTA TCA CAA 525                530                   535              540
          Arg Tyr Arg Val Arg Ile Arg Tyr Ala Ser Thr Thr Asn Leu Gln Phe His Thr Ser Ile
          AGA TAT CGC GTA AGA ATT CGC TAC GCT TCT ACT ACA AAT TTA CAA TTC CAT ACA TCA ATT 545                550                   555              560
          Asp Gly Arg Pro Ile Asn Gln Gly Asn Phe Ser Ala Thr Met Ser Ser Gly Gly Asn Leu
          GAC GGA AGA CCT ATT AAT CAG GGG AAT TTT TCA GCA ACT ATG AGT AGT GGG GGT AAT TTA 565                570                   575              580
          Gln Ser Gly Ser Phe Arg Thr Ala Gly Phe Thr Thr Pro Phe Asn Phe Ser Asn Gly Ser
          CAG TCC GGA AGC TTT AGG ACT GCA GGT TTT ACT ACT CCG TTT AAC TTT TCA AAT GGA TCA
```

Figure 7F

```
         585                   590                   595                   600
Ser Ile Phe Thr Leu Ser Ala His Val Phe Asn Ser Gly Asn Val Tyr Ile Asp Arg
AGT ATA TTT ACG TTA AGT GCT CAT GTC TTC AAT TCA GGC AAT GTT TAT ATA GAT CGA 605                   610                   615                   620
Ile Glu Phe Val Pro Ala Glu Val Thr Phe Glu Ala Glu Tyr Asp Leu Glu Arg Ala Gln
ATT GAA TTT GTT CCG GCA GAA GTA ACA TTT GAG GCG GAA TAT GAT TTA GAA AGA GCG CAA 625                   630                   635                   640
Glu Ala Val Asn Ala Leu Phe Thr Ser Asn Gln Leu Gly Leu Lys Thr Asn Val Thr
GAG GCG GTG AAT GCT CTG TTT ACT TCT TCC AAT CAA CTA GGA TTA AAA ACA AAT GTG ACG 645                   650                   655                   660
Asp Tyr His Ile Asp Gln Val Ser Asn Leu Val Glu Cys Leu Ser Gly Glu Phe Cys Leu
GAC TAT CAT ATT GAT CAA GTG TCC AAT CTA GTC GAA TGT TTA TCC GGT GAA TTC TGT CTG 665                   670                   675                   680
Asp Glu Lys Arg Glu Leu Ser Glu Lys Val Lys His Ala Lys Arg Leu Ser Asp Glu Arg
GAT GAA AAG AGA GAA TTG TCC GAG AAA GTC AAA CAT GCG AAG CGA CTC AGT GAT GAG CGG
```

Figure 7G

```
                    685                    690                    695                    700
Asn Leu Leu Gln Asp Pro Asn Phe Arg Gly Ile Asn Arg Gln Pro Asp Arg Gly Trp Arg
AAT TTA CTT CAA GAC CCA AAC TTC AGA GGC ATC AAT AGA CAA CCA GAC CGT GGC TGG AGA 705                    710                    715                    720
Gly Ser Thr Asp Ile Thr Ile Gln Gly Asp Asp Val Phe Lys Glu Asn Tyr Val Thr
GGC AGT ACG GAT ATT ACC ATC CAA GGA GAT GAC GTA TTC AAA GAG AAT TAC GTC ACA 725                    730                    735                    740
Leu Pro Gly Thr Phe Asn Glu Cys Tyr Pro Thr Tyr Leu Tyr Gln Lys Ile Asp Glu Ser
CTA CCG GGT ACC TTT AAT GAG TGT TAT CCT ACG TAT CTG TAT CAA AAA ATA GAT GAG TCG 745                    750                    755                    760
Lys Leu Lys Ala Tyr Thr Arg Tyr Gln Leu Arg Gly Tyr Ile Glu Asp Ser Gln Asp Leu
AAA TTA AAA GCC TAT ACC CGT TAC CAA TTA AGA GGG TAC ATC GAG GAT AGT CAA GAC TTA 765                    770                    775                    780
Glu Ile Tyr Leu Ile Arg Tyr Asn Thr Lys His Glu Thr Val Asn Val Pro Gly Thr Gly
GAA ATC TAT TTA ATT CGC TAC AAT ACA AAA CAC GAA ACA GTA AAT GTG CCA GGT ACG GGT
```

Figure 7H

```
                        785                          790                          795                         800
Ser Leu Trp Pro Leu Ser Val Glu Asn Pro Ile Gly Lys Cys Gly Glu Pro Asn Arg Cys
TCC TTA TGG CCG CTT TCA GTC GAA AAT CCA ATT GGA AAG TGC GGA GAA CCA AAT CGA TGC 805                          810                          815                         820
Ala Pro Gln Leu Glu Trp Asn Pro Asp Leu Asp Cys Ser Cys Arg Asp Gly Lys Cys
GCA CCA CAA CTT GAA TGG AAT CCT GAT CTA GAT TGT TCC TGC AGA GAC GGG GAA AAA TGT 825                          830                          835                         840
Ala His His Ser His Phe Ser Leu Asp Ile Gly Cys Thr Asp Leu Asn Glu
GCA CAT CAC TCC CAT TTC TCC TTG GAC ATT GGA TGT ACA GAT TTA AAT GAG 845                          850                          855                         860
Asn Leu Gly Val Trp Val Ile Phe Lys Ile Lys Thr Gln Asp Gly His Ala Arg Leu Gly
AAC TTA GGT GTA TGG GTG ATA TTC AAA ATT AAG ACG CAA GAT GGT CAC GCA AGA CTA GGT 865                          870                          875                         880
Asn Leu Glu Phe Leu Glu Lys Pro Leu Val Gly Glu Ser Leu Ala Arg Val Lys Arg
AAT CTA GAG TTT CTC GAA AAA CCA TTA GTA GGC GAA TCG TTA GCA CGC GTG AAG AGA
```

Figure 7I

```
                                     885                      890                   895                      900
           Ala Glu Lys Lys Trp Arg Asp Lys Arg Glu Lys Leu Gln Val Glu Thr Asn Ile Val Tyr
           GCG GAG AAG AAG TGG AGA GAC AAA CGA GAG AAG TTG CAA GTG GAA ACA AAT ATC GTT TAT 905                      910                   915                      920
           Lys Glu Ala Lys Glu Ser Val Asp Ala Leu Phe Val Asn Ser Gln Tyr Asp Arg Leu Gln
           AAA GAG GCA AAA GAA TCT GTA GAT GCT TTA TTT GTG AAC TCT CAA TAT GAT AGA TTA CAA 925                      930                   935                      940
           Ala Asp Thr Asp Ile Ala Met Ile His Ala Ala Asp Lys Arg Val His Arg Ile Arg Glu
           GCG GAT ACC GAC ATC GCG ATG ATT CAT GCG GCA GAT AAA CGC GTT CAT CGA ATT CGA GAA 945                      950                   955                      960
           Ala Tyr Leu Pro Glu Leu Ser Val Ile Pro Gly Val Asn Ala Gly Ile Phe Glu Glu Leu
           GCA TAT CTT CCA GAG TTA TCT GTA ATT CCG GGT GTC AAT GCG GGC ATT TTT GAA GAA TTA 965                      970                   975                      980
           Glu Gly Arg Ile Phe Thr Ala Tyr Ser Leu Tyr Asp Ala Arg Asn Val Ile Lys Asn Gly
           GAG GGA CGT ATT TTC ACA GCC TAC TCT TTA TAT GAT GCG AGA AAT GTC ATT AAA AAT GGC
```

Figure 7J

```
                985                      990                      995                      1000
Asp Phe Asn Asn Gly Leu Ser Cys Trp Asn Val Lys Gly His Val Asp Val Glu Glu Gln
GAT TTC AAT AAT GGC TTA TCA TGC TGG AAC GTG AAA GGG CAT GTA GAT GTA GAA GAA CAA 1005                     1010                     1015                     1020
Asn Asn His Arg Ser Val Leu Val Val Pro Glu Trp Glu Ala Glu Val Ser Gln Glu Val
AAC AAC CAC CGT TCG GTT CTT GTT GTC CCG GAA TGG GAA GCA GAG GTG TCA CAA GAG GTT 1025                     1030                     1035                     1040
Arg Val Cys Pro Gly Arg Gly Tyr Ile Leu Arg Val Thr Ala Tyr Lys Glu Gly Tyr Gly
CGT GTC TGT CCA GGT CGT GGC TAT ATC CTA CGT GTT ACA GCG TAC AAA GAG GGA TAT GGA 1045                     1050                     1055                     1060
Glu Gly Cys Val Thr Ile His Glu Ile Glu Asp Asn Thr Asp Glu Leu Lys Phe Ser Asn
GAA GGT TGC GTA ACG ATT CAT GAG ATC GAA GAC AAT ACA GAC GAA CTG AAA TTC AGC AAC 1065                     1070                     1075                     1080
Cys Val Glu Glu Val Tyr Pro Asn Asn Thr Val Thr Cys Asn Asp Tyr Thr Ala Asn
TGT GTA GAA GAG GTA TAT CCA AAC AAC ACG GTA ACG TGT AAT GAT TAT ACT GCA AAT
```

Figure 7K

```
              1085              1090              1095              1100
Gln Glu Glu Tyr Gly Gly Ala Tyr Thr Ser Arg Asn Arg Gly Tyr Gly Glu Ser Tyr Glu
CAA GAA GAA TAC GGG GGT GCG TAC ACT TCT CGT AAT CGT GGA TAT GGT GAA TCT TAT GAA 1105              1110              1115              1120
Ser Asn Ser Ser Ile Pro Ala Glu Tyr Ala Pro Val Tyr Glu Glu Ala Tyr Ile Asp Gly
AGT AAT TCT TCC ATA CCA GCT GAG TAT GCG CCA GTT TAT GAG GAA GCA TAT ATA GAT GGA 1125              1130              1135              1140
Arg Lys Glu Asn Pro Cys Glu Ser Asn Arg Gly Tyr Gly Asp Tyr Thr Pro Leu Pro Ala
AGA AAA GAG AAT CCT TGT GAA TCT AAC AGA GGA TAT GGG GAT TAC ACG CCA CTA CCA GCT 1145              1150              1155              1160
Gly Tyr Val Thr Lys Glu Leu Glu Tyr Phe Pro Glu Thr Asp Lys Val Trp Ile Glu Ile
GGT TAT GTG ACA AAA GAA TTA GAG TAC TTC CCA GAA ACC GAT AAG GTA TGG ATT GAG ATC 1165              1170              1175
Gly Glu Thr Glu Gly Thr Phe Ile Val Asp Ser Val Glu Leu Leu Leu Met Glu Glu
GGG GAA ACG GAA GGA ACA TTC ATC GTG GAT AGC GTG GAA TTA CTC CTT ATG GAG GAA
```

Figure 7L

GENES ENCODING LEPIDOPTERAN-ACTIVE TOXINS AND TRANSFORMED HOSTS

CROSS REFERENCE TO A RELATED APPLICATION

This is a division of application Ser. No. 07/451,389, filed Dec. 14, 1989, now U.S. Pat. No. 5,164,180 which is a continuation-in-part of application Ser. No. 353,860, filed May 18, 1989, now abandoned.

BACKGROUND OF THE INVENTION

The most widely used microbial pesticides are derived from the bacterium *Bacillus thuringiensis*. This bacterial agent is used to control a wide range of leaf-eating caterpillars and beetles, as well as mosquitos. *Bacillus thuringiensis* produces a proteinaceous parasporal body or crystal which is toxic upon ingestion by a susceptible insect host. For example, *B. thuringiensis* subsp. *kurstaki* HD-1 produces a crystal inclusion consisting of a biotoxin called a delta toxin which is toxic to the larvae of a number of lepidopteran insects. The cloning, sequencing, and expression of this *B.t.* crystal protein gene in *Escherichia coli* has been described in the published literature (Schnepf, H. E. and Whitely, H. R. [1981] Proc. Natl. Acad. Sci. USA 78:2893–2897; Schnepf et al.). U.S. Pat. Nos. 4,448,885 and 4,467,036 both disclose the expression of *B.t.* crystal protein in *E. coli*.

BRIEF SUMMARY OF THE INVENTION

The subject invention concerns novel *Bacillus thuringiensis* isolates designated *B.t.* PS81A2 and PS81RR1 which have activity against all lepidopteran pests tested.

Also disclosed and claimed are novel toxin genes which express toxins toxic to lepidopteran insects. These toxin genes can be transferred to suitable hosts via a plasmid vector.

Specifically, the invention comprises novel *B.t.* isolates denoted *B.t.* PS81A2 and PS81RR1, mutants thereof, and novel delta endotoxin genes derived from these *B.t.* isolates which encode proteins which are active against lepidopteran pests. More specifically, the gene in *B.t.* PS81A2 encodes a 133,601 dalton endoxin, whereas the gene in *B.t.* PS81RR1 encodes a 133,367 dalton endotoxin.

BRIEF DESCRIPTION OF THE DRAWINGS

FIG. 2 (parts a-d) discloses the DNA encoding the novel toxin expressed by PS81A2.

FIG. 3 (parts a-e) discloses the amino acid sequence of the novel toxin expressed by PS81A2.

FIG. 4 (parts a-l) is a composite of FIGS. 2 and 3.

FIG. 5 (parts a-e) discloses the DNA encoding the novel toxin expressed by PS81RR1.

FIG. 6 (parts a-f) discloses the amino acid sequence of the novel toxin expressed by PS81RR1.

FIG. 7 (parts a-l) is a composite of FIGS. 5 and 6.

DETAILED DISCLOSURE OF THE INVENTION

Figure 1:
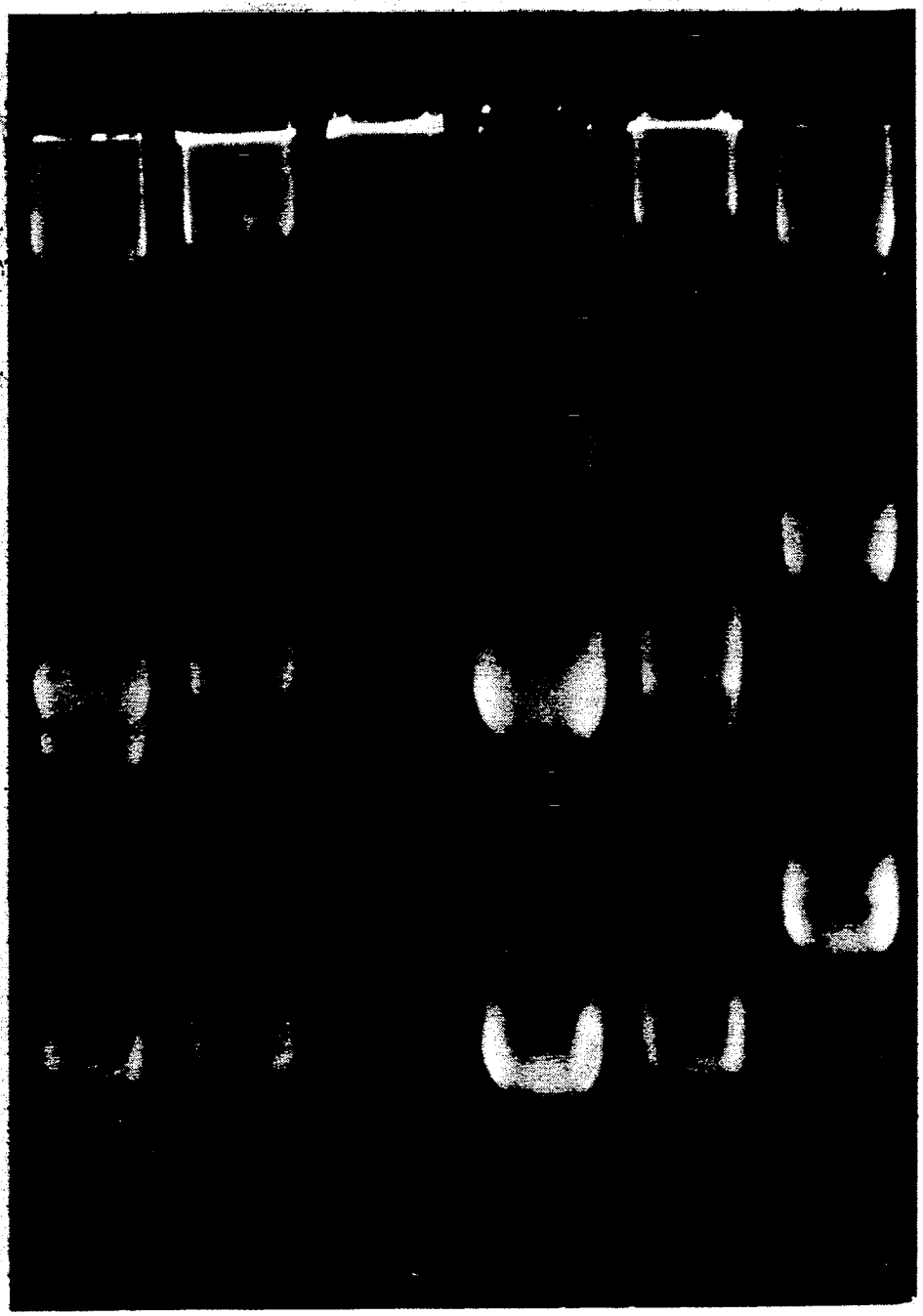
FIG. 1 shows agarose gel electrophoresis of plasmid preparations from *B.t.* PS81A2, *B.t.* PS81RR1, and *B.t.* HD-1.

The novel toxin genes of the subject invention were obtained from novel lepidopteran-active *B. thuringiensis* (*B.t.*) isolates designated PS81A2 and PS81RR1. Characteristics of *B.t.* PS81A2 and PS81RR1

Colony morphology—Large colony, dull surface, typical *B.t.*

Vegetative cell morphology—typical *B.t.*

Flagellar serotype—7, aizawai.

Intracellular inclusions—sporulating cells produce a bipyramidal crystal.

Plasmid preparations—agarose gel electrophoresis of plasmid preparations distinguishes *B.t.* PS81A2 and PS81RR1 from *B.t.* HD-1 and other *B.t.* isolates. See FIG. 1.

Alkali-soluble proteins—*B.t.* PS81A2 and PS81RR1 produce 133,601 and 133,367 dalton proteins, respectively.

Unique toxins—the 133,601 and 133,367 dalton toxins different from any previously identified.

Activity—*B.t.* PS81A2 and PS81RR1 both kill all Lepidoptera tested (*Trichoplusia ni, Spodoptera exigua,* and *Plutella xylostella*).

Bioassay procedures:

*Spodoptera exigua*—Dilutions are prepared of a spore and crystal pellet, mixed with USDA Insect Diet (Technical Bulletin 1528, U.S. Department of Agriculture) and poured into small plastic trays. Neonate *Spodoptera exigua* larvae are placed on the diet mixture and held at 25° C. Mortality is recorded after six days.

Other insects—Dilutions and diet are prepared in the same manner as for the *Spodoptera exigua* bioassay. Fourth instar larvae are used, and mortality is recorded after eight days.

*B. thuringiensis* PS81A2, NRRL B-18457, and *B. thuringiensis* PS81RR1, NRRL B-18458, and mutants thereof, can be cultured using standard known media and fermentation techniques. Upon completion of the fermentation cycle, the bacteria can be harvested by first separating the *B.t.* spores and crystals from the fermentation broth by means well known in the art. The recovered *B.t.* spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art and are used with commercial strains of *B. thuringiensis* (HD-1) active against *Lepidoptera*, e.g., caterpillars. *B.t.* PS81A2 and *B.t.* PS81RR1, and mutants thereof, can be used to control lepidopteran pests.

A subculture of *B.t.* PS81A2 and PS81RR1 and the *E. coli* hosts harboring the toxin genes of the invention, were deposited in the permanent collection of the Northern Research Laboratory, U.S. Department of Agriculture, Peoria, Ill., U.S.A. The accession numbers and deposit dates are as follows:

| Subculture | Accession Number | Deposit Date |
| --- | --- | --- |
| B.t. PS81A2 | NRRL B-18457 | March 14, 1989 |
| B.t. PS81RR1 | NRRL B-18458 | March 14, 1989 |
| E. coli (NM522) (pMYC389) | NRRL B-18448 | February 24, 1989 |
| E. coli (NM522) (pMYC390) | NRRL B-18449 | February 24, 1989 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

The toxin genes of the subject invention can be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of lepidopteran insects where they will proliferate and be ingested by the insects. The result is a control of the unwanted insects. Alternatively, the microbe hosting the toxin gene can be treated under conditions that prolong the activity of the toxin produced in the cell. The treated cell then can be applied to the environment of target pest(s). The resulting product retains the toxicity of the *B.t.* toxin.

Where the *B.t.* toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Bacillus, Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are available for introducing a *B.t.* gene expressing a toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organisms, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger RNA, particularly by using an active promoter, as well as by employing sequences, which enhance the stability of the messenger RNA. The transcriptional and translational termination region will involve stop codon(s), a terminator region, and optionally, a polyadenylation signal. A hydrophobic "leader" sequence may be employed at the amino terminus of the translated polypeptide sequence in order to promote secretion of the protein across the inner membrane.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a sideophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 1000 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the Tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pRO1614, and the like. See for example, Olson et al., (1982) J. Bacteriol. 150:6069, and Bagdasarian et al., (1981) Gene 16:237, and U.S. Pat. Nos. 4,356,270, 4,362,817, and 4,371,625.

The *B.t.* gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and- positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae, Actinomycetales, and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the *B.t.* gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., Streptomyces sp., and the like. Specific organisms include *Pseudomonas aeruginosa, Pseudomonas fluorescens, Saccharomyces cerevisiae, Bacillus thuringiensis, Escherichia coli, Bacillus subtilis, Streptomyces lividans* and the like.

The cell will usually be intact and be substantially in the proliferative form when treated, rather than in a spore form, although in some instances spores may be employed.

Treatment of the microbial cell, e.g., a microbe containing the *B.t.* toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Lugol iodine, Bouin's fixative, and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the *B.t.* insecticidal gene may be grown in any convenient nutrient medium, where the DNA construct provides a selective advantage, providing for a selective medium so that substantially all or all of the cells retain the *B.t.* gene. These cells may then be harvested in accordance with conventional ways. Alternatively, the cells can be treated prior to harvesting.

The *B.t.* cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the solid phase. The formulations will generally have from about $10^2$ to about $10^4$ cells/mg. These formulations will be administered at about 50 mg (liquid or dry) to 1 kg or more per hectare.

The formulations can be applied to the environment of the lepidopteran pest(s), e.g., plants, soil or water, by spraying, dusting, sprinkling, or the like.

Mutants of PS81A2 and PS81RR1 can be made by procedures well known in the art. For example, an asporogenous mutant can be obtained through ethylmethane sulfonate (EMS) mutagenesis of PS81A2 and PS81RR1. The mutants can be made using ultraviolet light and nitrosoguanidine by procedures well known in the art.

A smaller percentage of the asporogenous mutants will remain intact and not lyse for extended fermentation periods; these strains are designed lysis minus (−). Lysis minus stains can be identified by screening asporogenous mutants in shake flask media and selecting those mutants that are still intact and contain toxin crystals at the end of the fermentation. Lysis minus are suitable for a cell fixation process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive is also plated in the same manner to serve as the positive control. After drying, a drop of the phage lysate is plated in the center of the plate and allowed to dry. Resistant cultures showed no lysis in the area where the phage lysate has been placed after incubation at 30° C. for 24 hours.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing *B.t.* PS81A2 and PS81RR1

A subculture of *B.t.* PS81A2 and PS81RR1, or mutants thereof, can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| Salts Solution (100 ml) | |
| $MgSO_4 \cdot 7H_2O$ | 2.46 g |
| $MnSO_4 \cdot H_2O$ | 0.04 g |
| $ZnSO_4 \cdot 7H_2O$ | 0.28 g |
| $FeSO_4 \cdot 7H_2O$ | 0.40 g |
| $CaCl_2$ Solution (100 ml) | |
| $CaCl_2 \cdot 2H_2O$ | 3.66 g |

-continued pH 7.2

The salts solution and CaCl₂ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The *B.t.* spores and/or crystals, obtained in the above fermentation, can be isolated by procedures well known in the art. A frequently-used procedure is to subject the harvested fermentation broth to separation techniques, e.g., centrifugation.

EXAMPLE 2

Cloning of Novel Toxin Gene From Isolate PS81A2 and Transformation Into *Escherichia coli*

Total cellular DNA was prepared from *B.t.* cells grown to a low optical density (OD₆₀₀=1.0). The cells were recovered by centrifugation and protoplasted in TES buffer (30 mM Tris-Cl, 10 mM ethylenediaminetetraacetic acid [EDTA], 50 mM NaCl, pH=8.0) containing 20% sucrose and 50 mg/ml lysozyme. The protoplasts were lysed by addition of sodium dodecyl sulfate (SDS) to a final concentration of 4%. The cellular material was precipitated overnight at 4° C. in 100 mM (final concentration) neutral potassium chloride. The supernate was extracted twice with phenol/chloroform (1:1). The DNA was precipitated with ethanol and purified by isopycnic banding on a cesium gradient.

Total cellular DNA from PS81A2 and B.t.k. HD-1 was digested with EcoRI and separated by electrophoresis on a 0.8% Agarose-TAE-buffered gel. A Southern blot of the gel was probed with the NsiI to NsiI fragment of the toxin gene contained in plasmid pM3,130-7 of NRRL B-18332 and the NsiI to KpnI fragment of the "4.5 Kb class" toxin gene (Kronstad and Whitely [1986] Gene USA 43:29–40). These two fragments were combined and used as the probe. Results show that hybridizing fragments of PS81A2 are distinct from those of HD-1. Specifically, a 3.0 Kb hybridizing band in PS81A2 was detected instead of the 3.8 Kb and 1.8 Kb hybridizing bands seen in HD-1.

Two hundred micrograms of PS81A2 total cellular DNA was digested with EcoRI and separated by electrophoresis on a preparative 0.8% Agarose-TAE gel. The 2.5 Kb to 3.5 Kb region of the gel was cut out and the DNA from it was electroeluted and concentrated using an ELUTIP™-d (Schleicher and Schuell, Keene, N.H.) ion exchange column. The isolated EcoRI fragments were ligated to LAMBDA ZAP™ EcoRI arms (Stratagene Cloning Systems, La Jolla, Calif.) and packaged using Gigapak GOLD™ (Stratagene) extracts. The packaged recombinant phage were plated with *E. coli* strain BB4 (Stratagene) to give high plaque density. The plaques were screened by standard nucleic acid hybridization procedure with radiolabeled probe. The plaques that hybridized were purified and re-screened at a lower plaque density. The resulting purified phage were grown with R408 M13 helper phage (Stratagene) and the recombinant BlueScript™ (Stratagene) plasmid was automatically excised and packaged. The "phagemid" was re-infected in XL1-Blue *E. coli* cells (Stratagene) as part of the automatic excision process. The infected XL1-Blue cells were screened for ampicillin resistance and the resulting colonies were analyzed by standard miniprep procedure to fine the desired plasmid. The plasmid, designated pM6,31-1, contains an approximate 3.0 Kb EcoRI insert and was sequenced using Stratagene's T7 and T3 primers plus a set of existing *B.t.* endotoxin gene oligonucleotide primers. About 1.8 Kb of the toxin gene was sequenced, and data analysis comparing PS81A2 to other cloned *B.t.* endotoxin genes showed that the PS81A2 sequence was unique. A synthetic oligonucleotide (CAGATCCACGAGGCTTATCTTCCAGAACTAC) was constructed to one of the regions in the PS81A2 sequence that was least homologous relative to other exiting *B.t.* endotoxin genes.

PS81A2 total cellular DNA partially digested with Sau3A and fractionated by electrophoresis into a mixture of 9-23 Kb fragments on a 0.6% agarose-TAE gel was ligated into Lambda DASH ™ (Stratagene). The packaged phage at a high titer were plated on P2392 *E. coli* cells (Stratagene) and screened using the radiolabeled synthetic oligonucleotide (aforementioned) as a nucleic acid hybridization probe. Hybridizing plaques were rescreened at a lower plaque density. A single purified hybridizing plaque was used to infect P2392 *E. coli* cells in liquid culture for preparation of phage for DNA isolation DNA was isolated by standard procedures. Preparative amounts of recombinant phage DNA were digested with SalI (to release the inserted DNA from lambda arms) and separated by electrophoresis on a 0.6% Agarose-TAE gel. The large fragments, electroeluted and concentrated as described above, were ligate top SalI-digested and dephosphorylated pUC19 (NEB). The ligation mixture was introduced by transformation into *E. coli* DH5(alpha) competent cells (BRL) and plated on LB agar containing ampicillin, isopropyl-(Beta)-D-thiogalactoside (IPTG) and 5-Bromo-4-Chloro-3-indolyl-(Beta)-D-galactoside (XGAL). White colonies (with insertions in the (Beta)-galactosidase gene of pUC19) were subjected to standard miniprep procedures to isolate the plasmid, designated pM4,122-3. The full length toxin gene was sequenced by using oligonucleotide primers made to the "4.5 Kb class" toxin gene and by "walking" with primers made to the sequence of PS81A2.

The plasmid pM4,122-3 contains about 15 Kb of PS81A2 DNA including the 3.522 Kb which encodes the 133,601 dalton endotoxin. The ORF of the PS81A2 toxin gene was isolated from pM4,122-3 and subcloned into the Bacillus shuttle vector PBClac as a 5.5 Kb blunt-ended DraIII fragment. *E. coli* NM522 cells were transformed and plated on LB agar supplemented with ampicillin. The resulting colonies were analyzed by standard miniprep procedures to isolate plasmids that contained the insert. The desired plasmid, pMYC389, contains the coding sequence of the PS81A2 toxin gene.

EXAMPLE 3

Cloning of Novel Toxin Gene From Isolate PS81RR1 and Transformation into *Escherichia coli*

Total cellular DNA was prepared from *B.t.* cells grown to a low optical density (OD₆₀₀=1.0). The cells were recovered by centrifugation and protoplasted in TES buffer (30 mM Tris-Cl, 10 mM ethylenediaminetetraacetic acid [EDTA], 50 mM NaCl, pH=8.0) containing 20% sucrose and 50 mg/ml lysozyme. The protoplasts were lysed by addition of sodium dodecyl sulfate (SDS) to a final concentration of 4%. The cellular material was precipitated overnight at 4° C. in 100 mM (final concentration) neutral potassium chloride. The supernate was extracted twice with phenol/chloroform (1:1). The DNA was precipitated with ethanol and purified by isopycnic banding on a cesium chloride gradient.

Total cellular DNA from PS81RR1 and B.t.k. HD-1 was digested with EcoRI and separated by electrophoresis on a 0.8% Agarose-TAE-buffered gel. A Southern blot of the gel was probed with the NsiI to NsiI fragment of the toxin gene contained in plasmid pM3,130-7 of NRRL B-18332 and the NsiI to KpnI fragment of the "4.5 Kb class" toxin gene (Kronstad and Whitely [1986] Gene USA 43:29–40). These two fragments were combined and used as the probe. Results show that hybridizing fragments of PS81RR1 are distinct from those of HD-1. Specifically, a 2.3 Kb hybridizing band in PS81RR1 was detected instead of the 3.8 Kb and 1.8 Kb hybridizing bands seen in HD-1.

Two hundred micrograms of PS81RR1 total cellular DNA was digested with EcoRI and separated by electrophoresis on a preparative 0.8% Agarose-TAE gel. The 2.2 Kb to 2.4 Kb region of the gel was cut out and the DNA from it was electroeluted and concentrated using an ELUTIP TM -d (Schleicher and Schuell, Keene, NH) ion exchange column. The isolated RcoRI fragments were ligated to LAMBDA ZAP TM EcoRI arms (Stratagene Cloning Systems, La Jolla, Calif.) and packaged using Gigapak GOLD TM (Stratagene) extracts. The packaged recombinant phage were plated with E. coli strain BB4 (Stratagene) to give high plaque density. The plaques were screened by standard nucleic acid hybridization procedure with radiolabeled probe. The plaques that hybridized were purified and rescreened at a lower plaque density. The resulting purified phage were grown with R408 M13 helper phage (Stratagene) and the recombinant BlueScript TM (Stratagene) plasmid was automatically excised and packaged. The "phagemid" was re-infected in XL-1-Blue E. coli cells (Stratagene) as part of the automatic excision process. The infected XL1-Blue cells were screened for ampicillin resistance and the resulting colonies were analyzed by standard miniprep procedure to find the desired plasmid. The plasmid, designated pM3,31-3, contains an approximate 2.3 Kb EcoRI insert and was sequenced using Stratagene's T7 and T3 primers plus a set of existing B.t. endotoxin oligonucleotide primers. About 600 bp of the toxin gene was sequenced, and data analysis comparing PS81RR1 to other cloned B.t. endotoxin genes showed that the PS81RR1 sequence was unique. A synthetic oligonucleotide (CGTGGATATGGTGAATCTTATG) was constructed to one of the regions in the PS81RR1 sequence that was least homologous relative to other existing B.t. endotoxin genes.

PS81RR1 total cellular DNA partially digested with Sau3A and fractionated by electrophoresis into a mixture of 9-23 Kb fragments on a 0.6% agarose-TAE gel was ligated into Lambda GEM TM -11 (PROMEGA). The packaged phage at a high titer were plated on P2392 E. coli cells (Stratagene) and screened using the radiolabeled synthetic oligonucleotide (aforementioned) as a nucleic acid hybridization probe. Hybridizing plaques were rescreened at a lower plaque density. A single purified hybridizing plaque was used to infect P2392 E. coli cells in liquid culture for preparation of phage for DNA isolation. DNA was isolated by standard procedures. Preparative amounts of recombinant phage DNA were digested with SalI, to release the inserted DNA from lambda arms, and separated by electrophoresis on a 0.6% Agarose-TAE gel. The large fragments, electroeluted and concentrated as described above, were ligated to SalI-digested and dephosphorylated pUC19 (NEB). The ligation mixture was introduced by transformation into E. coli HD5(alpha) competent cells (BRL) and plated on LB agar containing ampicillin, isopropyl-(Beta)-D-thiogalactoside (IPTG) and 5-Bromo-4-Chloro-3-indolyl-(Beta)-D-galactoside (XGAL). White colonies (with insertions in the (Beta)-galactosidase gene of pUC19) were subjected to standard miniprep procedures to isolate the plasmid, designated pM1,RR1-A. The full length toxin gene was sequenced by using oligonucleotide primers made to the "4.5 Kb class" toxin gene and by "walking" with primers made to the sequence of PS81RR1.

The plasmid pM1,RR1-A contains about 13 Kb of PS81R1 DNA including the 3.540 Kb which encodes the 133,367 dalton endotoxin. The ORF of the PS81RR1 toxin gene was isolated from pM1,RR1-A on a 3.8 Kb NdeI fragment and ligated into the Bacillus shuttle vector pBClac. E. coli NM522 cells were transformed and the resulting colonies were analyzed by standard miniprep procedures to isolate plasmids that contained the correct insert. The desired plasmid, pMYC390, contains the coding sequence of the PS81RR1 toxin gene.

The above cloning procedures were conducted using standard procedures unless otherwise noted.

The various methods employed in the preparation of the plasmids and transformation of host organisms are well known in the art. Also, methods for the use of lambda bacteriophage as a cloning vehicle, i.e., the preparation of lambda DNA, in vitro packaging, and transfection of recombinant DNA, are well known in the art. These procedures are all described in Maniatis, T., Fritsch, E. F., and Sambrook, J. (1982) *Molecular Cloning: A laboratory Manual*, Cold Springs Harbor Laboratory, N.Y. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

The restriction enzymes disclosed herein can be purchased from Bethesda Research Laboratories, Gaithersburg, Md., New England Biolabs, Beverly, Mass., or Boehringer-Mannheim, Indianapolis, Ind. The enzymes are used according to the instructions provided by the supplier.

Plasmid pMYC386 containing the B.t. toxin genes, can be removed from the transformed host microbes by use of standard well-known procedures. For example, E. coli NRRL B-18449 can be subjected to cleared lysate isopycnic density gradient procedures, and the like, to recover pMYC386.

EXAMPLE 4

Insertion of Toxin Genes Into Plants

The novel genes coding for the novel insecticidal toxins, as disclosed herein, can be inserted into plant cells using the Ti plasmid from *Agrobacter tumefaciens*. Plant cells can then be caused to regenerate into plants (Zambryski, P., Joos, H., Gentello, C., Leemans, J., Van Montague, M. and Schell, J [1983] Cell 32:1033–1043). A particularly useful vector in this regard is pEND4K (Klee, H. J., Yanofsky, M. F. and Nester, E. W. [1985] Bio/Technology 3:637–642). This plasmid can replicate both in plant cells and in bacteria and has multiple cloning sites for passenger genes. The toxin gene, for example, can be inserted into the BamHI site of pEND4K, propagated in *E. coli*, and transformed into appropriate plant cells.

EXAMPLE 5

Cloning of Novel *B. thuringiensis* Genes Into Baculoviruses

The novel genes of the invention can be cloned into baculoviruses such as *Antographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miller, L. K. [1984] Mol. Cell. Biol. 4:399–406), and pAC380, described by Smith et al. (Smith, G. E., Summers, M. D. and Fraser, M. J. [1983] Mol. Cel. Biol. 3:2156–2165). The gene coding for the novel protein toxin of the invention can be modified with BamHI linkers at appropriate regions both upstream and downstream from the coding region and inserted into the passenger site of one of the AcNPV vectors.

As disclosed previously, the nucleotide sequences encoding the novel *B.t.* toxin genes are shown in FIGS. 2 and 5. The deduced amino acid sequence are shown in FIGS. 3 and 6.

It is well known in the art that the amino acid sequence of a protein is determined by the nucleotide sequence of the DNA., Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| | | | |
|---|---|---|---|
| Phenylalanine (Phe) | TTK | Histidine (His) | CAK |
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3-letter deoxynucleotide triplet corresponds to a trinucleotide of mRNA, having a 5'-end on the left and a 3'-end on the right. All DNA sequences given herein are those of the strand whose sequence correspond to the mRNA sequence, with thymine substituted for uracil. The letters stand for the purine or pyrimidine bases forming the deoxynucleotide sequence.
A = adenine
G = guanine
C = cytosine
T = thymine
X = T or C if Y is A or G -continued X = C if Y is C or T
Y = A, G, C or T if X is C
Y = A or G if X is T
W = C or A if Z is A or G
W = C if Z is C or T
Z = A, G, C or T if W is C
Z = A or G if W is A
QR = TC if S is A, G, C or T; alternatively
QR = AG if S is T or C
J = A or G
K = T or C
L = A, T, C or G
M = A, C or T The above shows that the novel amino acid sequence of the *B.t.* toxins can be prepared by equivalent nucleotide sequences encoding the same amino acid sequence of the protein. Accordingly, the subject invention includes such equivalent nucleotide sequences. In addition it has been shown that proteins of identified structure and function may be constructed by changing the amino acid sequence if such changes do not alter the protein secondary structure (Kaiser, E. T. and Kezdy, F. J. [1984] Science 223:249–255). Thus, the subject invention includes mutants of the amino acid sequence depicted herein which do not alter the protein secondary structure, or fi the structure is altered, the biological activity is retained to some degree.

We claim:

1. Isolated DNA encoding a *Bacillus thuringiensis* toxin having the amino acid sequences shown in FIG. 3 or FIG. 6.

2. DNA, according to claim 1, having the nucleotide sequences shown in FIG. 2 or FIG. 5, respectively.

3. A recombinant DNA transfer vector comprising DNA having all or part of the nucleotide sequence which codes for the amino acid sequence shown in FIG. 3 or FIG. 6.

4. The DNA transfer vector, according to claim 3, transferred to and replicated in a prokaryotic or eukaryotic host.

5. A bacterial host transformed to express a *Bacillus thuringiensis* toxin having the amino acid sequence shown in FIG. 3 or FIG. 6.

6. *Escherichia coli*, according to claim 5, transformed with a plasmid vector containing the *Bacillus thuringiensis* toxin gene encoding the *Bacillus thuringiensis* toxin having the amino acid sequence shown in FIG. 3 or FIG. 6.

7. *Escherichia coli* host according to claim 5, selected from the group consisting of *Escherichia coli* (NM522) (pMYC389) having the identifying characteristics of NRRL B-18448 and *Escherichia coli* (NM522) (pMYC390) having the identifying characteristics of NRRL-B-18449.

8. A bacterial host according to claim 5, which is a species of Pseudomonas, Azotobacter, Erwinia, Serratia, Klebsiella, Rhizobium, Rhodopseudomonas, Methylophilius, Agrobacterium, Acetobacter, Alcaligenes, Bacillus or Streptomyces.

9. A bacterial host according to claim 8, wherein said bacterial host is pigmented and phylloplane adherent.

10. Plasmid denoted pMYC389 or pMYC390, according to claim 4.

* * * * *

UNITED STATES PATENT AND TRADEMARK OFFICE
CERTIFICATE OF CORRECTION

PATENT NO. : 5,206,166

DATED : April 27, 1993

INVENTOR(S) : Jewel Payne and August J. Sick

Page 1 of 2

It is certified that error appears in the above-indentified patent and that said Letters Patent is hereby corrected as shown below:

Column 2, lines 15 and 16, "toxins different" should read --toxins are different--.

Column 5, line 22: "at least about 1000 bp" should read --at least about 100 bp--.

Column 6, line 19: "cells do not" should read --cells which do not--.

Column 7, line 64: "solids in solid phase" should read --solids in liquid phase--.

Column 8, line 13: "designed" should read --designated--; line 14: "stains" should read --strains--; line 17: "Lysis minus are" should read -Lysis minus strains are--; line 38: "The sensitive is also" should read --The sensitive strain is also--.

Column 10, line 2: "fine" should read --find--; line 25: "DNA isolation DNA" should read --DNA isolation. DNA--; line 31: "were ligate top" should read --were ligated to--; line 48: "PBC1ac" should read --pBC1ac--.

UNITED STATES PATENT AND TRADEMARK OFFICE
CERTIFICATE OF CORRECTION

PATENT NO. : 5,206,166
DATED : April 27, 1993
INVENTOR(S) : Jewel Payne and August J. Sick It is certified that error appears in the above-indentified patent and that said Letters Patent is hereby corrected as shown below:

Column 11, line 24: "RcoRI" should read --*Eco*RI--.

Column 12, line 5: "HD5" should read --DH5--; line 17: "PS81R1 DNA" should read --PS81RR1 DNA--.

Column 13, line 13: "*Antographa californica*" should read --*Autographa californica*--; line 34: "acid sequence" should read --acid sequences--; line 38: "DNA., Because" should read --DNA. Because--.

Column 14, line 26: "or fi the" should read --or if the--.

Signed and Sealed this

Eleventh Day of January, 1994

Attest:

BRUCE LEHMAN

*Attesting Officer*    Commissioner of Patents and Trademarks